(12) United States Patent
Upasani et al.

(10) Patent No.: US 6,780,853 B1
(45) Date of Patent: Aug. 24, 2004

(54) NEUROACTIVE STEROIDS OF THE ANDROSTANE AND PREGNANE SERIES

(75) Inventors: Ravindra B. Upasani, Foothill Ranch, CA (US); David B. Fick, Foothill Ranch, CA (US); Derk J. Hogenkamp, Carlsbad, CA (US); Nancy C. Lan, South Pasadena, CA (US)

(73) Assignee: Euro-Celtique S.A. (LU)

( * ) Notice: Subject to any disclaimer, the term of this patent is extended or adjusted under 35 U.S.C. 154(b) by 0 days.

(21) Appl. No.: 09/321,882

(22) Filed: May 28, 1999

Related U.S. Application Data

(60) Division of application No. 08/659,192, filed on Jun. 9, 1996, now Pat. No. 5,925,630, which is a continuation-in-part of application No. 08/467,404, filed on Jun. 6, 1995, now abandoned.

(51) Int. Cl.[7] ............................ A61K 31/58; C07J 43/00
(52) U.S. Cl. ...................................... 514/176; 540/111
(58) Field of Search ....................... 540/111; 552/553, 552/554, 556, 600, 603; 514/176

(56) References Cited

U.S. PATENT DOCUMENTS

| | | | |
|---|---|---|---|
| 3,135,744 A | 6/1964 | Ercoli et al. | 260/239.55 |
| 3,316,146 A | 4/1967 | Wechter | 167/52 |
| 3,822,298 A | 7/1974 | Clayton et al. | 260/397.4 |
| 3,882,151 A | 5/1975 | Phillipps et al. | 260/397.45 |
| 3,883,569 A * | 5/1975 | Phillipps et al. | 260/397.45 |
| 3,943,124 A | 3/1976 | Phillipps et al. | 260/239.55 R |
| 3,953,429 A | 4/1976 | Cook et al. | 260/239.55 |
| 3,959,260 A * | 5/1976 | Phillipps et al. | 260/239.5 |
| 3,969,345 A * | 7/1976 | Phillipps et al. | 260/239.55 |
| 3,998,829 A | 12/1976 | Phillips et al. | 260/239.5 |
| 4,192,871 A | 3/1980 | Phillipps et al. | 424/241 |
| 4,197,296 A | 4/1980 | Phillipps et al. | 424/241 |
| 4,297,350 A | 10/1981 | Babcock et al. | 424/238 |
| 5,120,723 A | 6/1992 | Gee et al. | 514/176 |
| 5,208,227 A | 5/1993 | Gee et al. | 514/172 |
| 5,232,917 A * | 8/1993 | Bolger et al. | 514/176 |
| 5,319,115 A | 6/1994 | Tahir et al. | 552/609 |
| 5,591,733 A | 1/1997 | Bolger et al. | 514/172 |
| 5,939,545 A | 8/1999 | Upasani et al. | 540/110 |

FOREIGN PATENT DOCUMENTS

| | | |
|---|---|---|
| DE | 1 050 765 | 8/1959 |
| DE | 2 156 094 | 5/1972 |
| FR | 1849 M | 6/1963 |
| FR | 1437361 | 3/1966 |
| GB | 839911 | 6/1960 |
| GB | 1 380 248 | 1/1975 |
| GB | 1 432 135 | 4/1976 |
| GB | 1 581 235 | 12/1980 |
| WO | WO 93/03732 | 3/1993 |
| WO | 94/27608 | * 12/1994 |
| WO | WO 94/27608 | 12/1994 |
| WO | WO 95/21617 | 8/1995 |
| WO | WO 96/16076 | 5/1996 |

OTHER PUBLICATIONS

Hosoda, H. et al., "Chemical Conversion of Corticosteroids to 3α,5α–Tetrahydro Derivatives. Synthesis of Allotetrahydro–11–deoxycortisol Glucuronides," *Chem. Pharm. Bull.* 33:4281–4287 (1985).

Lawrence, D.K. and Gill, E.W., "Structurally Specific Effects of Some Steroid Anesthetics on Spin–Labeled Liposomes," *Molec. Pharmacol.* 11:280–286, Academic Press (1975).

Atkinson, R.M. et al., "Action of Some Steroids on the Central Nervous System of the Mouse. II. Pharmacology," *J. Med. Chem.* 8:426–432 (1965).

Atwal, K.S. et al., "On Cardioactive Steroids. VI The Synthesis of 17α–Methyl Cardenolides," *Hetercycles 19*: 641–646 (1982).

Bauer, P.E. et al., "A Synthesis of 3β–Hydroxy–5β, 14α–bufa–20, 22–dienolide from Deoxycorticosterone," *J. Org. Chem.* 48:34–39 (1983).

Buckett, W.R. et al., "Pancuronium Bromide and Other Steroidal Neuromuscular Blocking Agents Containing Acetylcholine Fragments," *J. Med. Chem. 16*:1116–1124 (1973).

Bull, J.R. and Hoadley, C., "Cycloaddition–Oxidative Cleavage Pathways to 14β–Formyl–19–norsteroids," *Tetrahedron Lett.* 35:6171–6174 (Aug. 1994).

(List continued on next page.)

*Primary Examiner*—Barbara P. Badio
(74) *Attorney, Agent, or Firm*—Sterne, Kessler, Goldstein & Fox P.L.L.C.

(57) ABSTRACT

The invention relates to 3α-hydroxy, 17-(un)substituted derivatives of the androstane series and 3α-hydroxy, 21-substituted derivatives of the pregnane series. These derivatives are capable of acting at a recently identified site on the GRC, thereby modulating brain excitability in a manner that will alleviate stress, anxiety, insomnia, mood disorders that are amenable to GRC-active agents (such as depression) and seizure activity. The steroid derivatives of this invention are those having the general structural Formula:

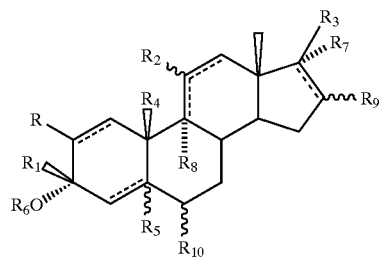

wherein R, $R_1$, $R_2$, $R_3$, $R_4$, $R_5$, $R_6$, $R_7$, $R_8$, $R_9$ and $R_{10}$ are farther defined herein and the dotted lines are single or double bonds. The structure includes androstanes, pregnanes ($R_4$=methyl), 19-norandrostanes, and norpregnanes ($R_4$=H).

9 Claims, 1 Drawing Sheet

OTHER PUBLICATIONS

Chanoine, F. et al., "Isolation and Identification of Major Metabolites of Tixocortol Pivalate in Human Urine," *Drug Metab. Disp.* 15:868–876 (1987).

Cocker, J.D. et al., "Action of some steroids on the central nervous system of the mouse. I. Synthetic methods," *Chem. Abstr.* 63: 4361f (1965).

Cocker, J.D. et al., "Action of Some Steroids on the Central Nervous System of the Mouse. I. Synthetic Methods," *J. Med. Chem.* 8:417–425 (1965).

Cross, A.D. et al., "Steroids CCLXXII. Biologically–Active Labile Ethers III. A New Class of Potent Estrogens," *Steroids* 5:557–583 (1965).

Draser, P. et al., "Alternative Synthesis of Steroidal Maleimides," *Collection Czechoslovak Chem. Comm.* 48:1224–1232 (183).

Engel, Ch.R. et al., "Favorsky Rearrangements of α–Halogenated Acetylcycloalkanes," *J. Org. Chem.* 47:4485–4491 (1982).

Ercoli, A. and Gardi, R., "17β–Alkenyloxyandrostanes," *Chem. Abstr.* 66:38147d (1967).

Falconi, G., "Steroid–17β–yl acetals and enol ethers: New orally active, C–17α not alkylated, anabolic compounds," *Chem. Abstr.* 64:17971f (1966).

Farmaceutici Italia Soc. Anon., "21–Triphenylmethyl ethers of corticosteroids," *Chem. Abstr.* 56:530h (1962).

Gee, K.W. and Yamamura, H.I., "Benzodiazepines and Barbiturates: Drugs for the Treatment of Anxiety, Insomnia, and Seizure Disorders, " in: *Drugs in Central Nervous System Disorders*, D.C. Horwell (Ed.), New York: Marcel Dekker, pp. 123–147 (1985).

Gee, K.W. et al., "GABA–dependent modulation of the CL' ionophore by steroids in rat brain," *Eur. J. Pharmacol.* 136:419–423 (1987).

Gee, K.W. et al., "Steroid Modulation of the Chloride Ionophore in Rat Brain: Structure–Activity Requirements, Regional Dependence and Mechanism of Action," *J. Pharmacol. Exp. Ther.* 246:803–821 (1988).

Grieco, P.A. and Stuk, T.L., "Remote Oxidation of Unactiviated C–H Bonds in Steroids via Oxometalloporphinates," *J. Am. Chem. Soc.* 112:7799–7801 (1990).

Harrison, N.L. et al., "Structure–Activity Relationships for Steroid Interaction with the γ–Aminobutyric Acid$_A$ Receptor Complex," *J. Pharmacol. Exp. Ther.* 241:346–353 (1987).

Hawkinson, J.E. et al., "Correlation of Neuroactive Steroid Modulation of [$^{35}$S] t–Butylbicyclophosphorothionate and [$^3$H] Flunitrazepam Binding and γ–Aminobutyric Acid$_A$ Receptor Function," *Molec. Pharmacol.* 46:977–985 (Nov. 1994).

Hu, Y. et al., "Neurosteroid Analogues: Structure–Activity Studies of Benz[e] indene Modulators of GABA$_A$ Receptor Function. 1. The Effect of 6–Methyl Substitution on the Electrophysiological Activity of 7–Substituted Benz[e]indene–3–carbonitriles," *J. Med. Chem.* 36:3956–3967 (1993).

Ihara, M. et al., "Steroselective Total Synthesis of Testosterone and Androsterone via A/B–Ring Construction of the Steroidal Ring System by Intramolecular Diels–Alder Reaction," *J. Chem. Soc. Perkins Trans. I*:117–123 (1986).

Im, W.B. et al., "Studies on the Mechanism of Interactions between Anesthetic Steroids and γ–Aminobutyric Acid–A Receptors," *Mol. Pharmacol.* 37:429–434 (1990).

Kirk, D.N. and Yeoh, B.L., "New Syntheses of 19,21–Dihydroxypregn–4–ene–3, 20–dione, 21–Hydroxy–19–norpregn–4–ene–3, 20–dione, and 11β,19,21–Trihydroxypregn–4–ene–3,20–dione," *J. Chem. Soc. Perkin Trans. I*:2945–2951 (1983).

Laboratories Français de Chimiothérapie, "Derivatives of etiocholane," *Chem. Abstr.* 55:619d (1961).

Lambert et al., "Actions of synthetic and endogenous steroids on the GABA$_A$ receptor," *Trends Pharmacol. Sci.* 8:224–227 (1987).

Lan, N.C. et al., "Identification and Characterization of a Pregnane Steroid Recognition Site That is Functionally Coupled to an Expressed GABA$_A$ Receptor," *Neurochem. Res.* 16:347–356 (1991).

Lalièvre, V. et al., "Correlation Between Binding Activity, Inhibition of Lymphoblastic Transformation and Metabolism of Tixocortol 21 Pivalate in Mouse Thymocytes," *Agents and Actions* 21:262–265 (1987).

Lawrence, D.K. and Gill, E.W., "Structurally specific effects of some steroid anesthetics on spin Labeled Liposome," *Chem. Abstr.* 84:54385g (1976).

Lewbart, M.L. and Mattox, V.R., "Oxidation of steroidal α–ketols to glyoxals with cupric acetate," *Chem. Abstr.* 59:6474c (1963).

Lewbart, M.L. and Mattox, V.R., "Oxidation of Steroidal α–Ketols to Glyoxals with Cupric Acetate," *J. Org. Chem.* 28: 2001–2006 (1963).

Lloyd, K.G. and Morselli, P.L., "Psychopharmacology of GABAergic Drugs," in: *Psychopharmacology: The Third Generation of Progress*, H.Y. Meltzer (Ed.), New York: Raven Press, pp. 183–195 (1987).

Majewska, M.D. et al., "Steroid Hormone Metabolites are Barbiturate–Like Modulators of the GABA Receptor," *Science* 232:1004–1007 (1986).

Neef, G. et al., "Reaction of Unsaturated Sulfoxides with Alkyllithiums," *Tetrahedron Lett.* 21:903–906 (1980).

Phillipps, G.H., "Structure–Activity Relationships in Steroidal Anaesthetics," *J. Steroid Biochem.* 6:607–613 (1975).

Phillipps, G.H., "Structure–Activity Relationships in Steroidal Anaesthetics," *Molecular Mechanisms in General Anesthesia*, Halsey, M.J. et al. (Eds.), Glaxo Syposium, pp. 32–47 (1974).

Purdy et al., "Synthesis, Metabolism and Pharmacological Activity of 3α–Hydroxy Steroids Which Potentiate GABA–Receptor–Mediated Chloride Ion Uptake in Rat Cerebral Cortical Synaptoneurosomes," *J. Med. Chem.* 33:1572–1581 (1990).

Re, L., "Reductive removal of the 17α–hydroxyl group of the cortical side–chain," *Chem. Abstr.* 60:1820d (1964).

Re, L., "Reductive Removal of the 17α–hydroxyl Group of the Cortical Side–Chain," *Steroids* 2:465–470 (1963).

Roussel—UCLAF, "Esters of 3α–hydroxyetiocholan–11–one," *Chem. Abstr.* 67:1916g (1969).

Rubin, M., "19–Methyl–19–acyloxystrophanthidins," *Chem. Abstr.* 59:11617b (1963).

Templeton, J.F. et al., "Stereoselective Reduction of C–2 Substituted Steroid C–3 Ketones with Lithium Tris–(R,S–1, 2–Dimethylpropyl)–Borohydride and Sodium Borohydride," *Steroids* 48:339–346 (1986).

Warnant, J. and Joly, R., "Testan–3α–ol–11–one and its esters," *Chem. Abstr.* 55:3660b (1961).

Wieland, S. et al., "Comparative Behavioral Characterization of the Neuroactive Steroids 3α–OH, 5α–pregan–20–one and 3α–OH, 5β–pregnan–20–one in Rodents," *Psychopharmacol.* 118:65–71 (Mar. 1995).

English abstract of French Patent Documents No. FR 1849M (Reference AN1), Derwent abstract No. 66–08474F/00 (1963).

English abstract of French Patent Document No. FR 1, 437, 361 (Reference A01), Derwent abstract No. 66–05905F/00 (1966).

International Search Report issued by PCT International Searching Authority for Application No. PCT/US96/10115, mailed Feb. 17, 1997.

Communication Relating to the Results of the Partial International Search issued by ISA/EPO for PCT/US96/10115, filed Jun. 6, 1996.

* cited by examiner

NEUROACTIVE STEROIDS OF THE ANDROSTANE AND PREGNANE SERIES

This application is a division of U.S. application Ser. No. 08/659,192, filed Jun. 6, 1996, now U.S. Pat. No. 5,925,630, which is a continuation-in-part of U.S. application Ser. No. 08/467,404, filed Jun. 6, 1995, abandoned, the contents of which is incorporated by reference herein.

BACKGROUND OF THE INVENTION

1. Field of the Invention

The present invention is directed to novel steroid derivatives of the androstane and pregnane series, as well as pharmaceutical compositions and methods for modulating brain excitability. More particularly, the invention relates to 3α-hydroxy, 17-(un)substituted derivatives of the androstane series and 21-substituted derivatives of the pregnane series.

2. Related Art

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately –80 mV, the cell interior being negative with respect to the cell exterior. The potential (voltage) is the result of ion ($K^+$, $Na^-$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from –80 mV to –50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium) produce their therapeutically useful effects by interacting with specific regulatory sites on the GRC.

Accumulated evidence has now indicated that in addition to the benzodiazepine and barbiturate binding site, the GRC contains a distinct site for neuroactive steroids (Lan, N. C. et at, *Neurochem. Res.* 16:347–356 (1991)). Neuroactive steroids can occur endogenously. The most potent endogenous neuroactive steroids are 3α-hydroxy-5-reduced pregnan-20-one and 3α,21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232:1004–1007 (1986); Harrison, N. L. et al., *J. Pharmacol. Exp. Ther.* 241:346–353 (1987)). However, the therapeutic usefulness of these steroid metabolites and their derivatives (neuroactive steroids) was not recognized by workers in the field due to an incomplete understanding of the potency and site of action of these neuroactive steroids. Applicants' invention relates in part to a pharmaceutical application of the knowledge gained from a more developed understanding of the potency and site of action of certain steroid compounds.

The ovarian hormone progesterone and its metabolites have been demonstrated to have profound effects on brain excitability (Backstrom, T. et al., *Acta Obstet. Gynecol. Scand. Suppl.* 130:19–24 (1985); Pfaff, D. W. and McEwen, B. S., *Science* 219:808–814 (1983); Gyermek et al., *J. Med. Chem.* 11:117 (1968); Lambert, J. et al., *Trends Pharmacol. Sci.* 8:224–227 (1987)). The levels of progesterone and its metabolites vary with the phases of the menstrual cycle. It has been well documented that progesterone and its metabolites decrease prior to the onset of menses. The monthly recurrence of certain physical symptoms prior to the onset of menses has also been well documented. These symptoms, which have become associated with premenstrual syndrome (PMS) include stress, anxiety, and migraine headaches (Dalton, K., *Premenstrual Syndrome and Progesterone Therapy*, 2nd edition, Chicago Yearbook, Chicago (1984)). Patients with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Ladlaw, J., *Lancet*, 1235–1237 (1956)). A more direct correlation has been observed with a reduction in progesterone metabolites (Rosciszewska et al., *J. Neurol. Neurosurg. Psych.* 49:47–51 (1986)). In addition, for patients with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8–20 (1983)). The steroid deoxycorticosterone has been found to be effective in treating patients with epileptic spells correlated with their menstrual cycles (Aird, R. B. and Gordan, G., *J. Amer. Med. Soc.* 145:715–719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants and women experiencing PND show an increased incidence of PMS (Dalton, K., *Premenstrual Syndrome and Progesterone Therapy*, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS and PND. The correlation between reduced levels of progesterone and the symptoms associated with PMS, PND, and catamenial epilepsy (Backstrom, T. et al., *J. Psychosom. Obstet. Gynaecol.* 2:8–20 (1983)); Dalton, K., *Premenstrual Syndrome and Progesterone Therapy*, 2nd edition, Chicago Yearbook, Chicago (1984)) has prompted the use of progesterone in their treatment (Mattson et al., "Medroxyprogesterone therapy of catamenial epilepsy," in *Advances in epileptology: XVth Epilepsy International Symposium*, Raven Press, New York (1984), pp. 279–282, and Dalton, K., *Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks, et al., *Obstet. Gynecol.* 154:573–581 (1986); Dennerstein, et al., *Brit. Med. J.* 290:16–17 (1986)).

Templeton et al., *Steroids* 48:339–346 (1986) discloses a stereoselective and regioselective reduction of steroid ketones to form axial alcohols at C-3. The compound 17β-methoxy-2β-methyl-5α-androstan-3α-ol is formed from 17β-methoxy-2α,3α-epoxy-5α-androstane.

Grieco et al., *J. Am. Chem. Soc.* 11:7799–7801 (1990) discloses the use of 17β-methoxy-5α-androstan-3α-ol as a starting material for forming conjugates comprising metalloporphyrins attached to steroid substrates.

Babcock et al., U.S. Pat. No. 4,297,350, issued Oct. 27, 1991, broadly discloses steroidal androstane and androstane 17-ethers and their use as male contraceptives.

Neef et al., *Tetrahedron Letters* 21:903–906 (1980) discloses the compound 17β-methoxymethoxy-3β-(1-propynyl)-5α-androsten-3α-ol as an intermediate in the formation of steroid derivatives.

FR 1,437,361, published May 6, 1966 and U.S. Pat. No. 3,135,744, issued Jun. 2, 1964, disclose the 17-(2-methyl-2-butenyl) and cycloalkenyl ethers of 5α-androstane-3α, 17β-diol and 3-lower alkanoyl esters thereof. The compounds are taught to have androgenic and/or anabolic activity.

Phillips et al, U.S. Pat. No. 4,197,296, issued Apr. 8, 1980, discloses steroids of the androstane series which possess a 3α-hydroxy group, a 5α- or 5β-hydrogen atom, and an 11α-substituted amino group wherein the 17 position may be unsubstituted. The compound 11α-N,N-dimethylamino-2β-ethoxy-5α-androstan-3α-ol is disclosed. The patent discloses that these compounds have anesthetic activity.

Phillips et al., U.S. Pat. No. 3,882,151, issued May 6, 1975, and Phillips et al., U.S. Pat. No. 3,969,345, issued Jul. 13, 1976, disclose 3α-oxygenated pregnane 21-ethers possessing a 3α-hydroxy group or an ester thereof, a keto group in the 20-position, and an etherified hydroxyl group in the 21-position. The 21-ether substituent is preferably an alkoxy, cycloalkoxy, aralkoxy, or aryloxy group that may carry additional substituents. The patents disclose that these compounds have anesthetic activity.

Phillips et al., U.S. Pat. No. 3,959,260, issued May 25, 1976, discloses steroid anesthetics of the pregnane and 19-norpregnane series which possess a 3α-hydroxy group, a 20-oxo group, and at the 21-position the residue of a sulfur containing nucleophile or a sulphone or sulfoxide grouping. The 3β-substituent may be either hydrogen or alkyl.

Clayton et al., U.S. Pat. No. 3,822,298, issued Jul. 2, 1974, discloses a process for preparing 3α-hydroxy-5α-steroids. The patent discloses the preparation of 21-benzyloxy-3α-hydroxy-5α-pregnane-11,20-dione.

SUMMARY OF THE INVENTION

The present invention is directed to novel steroid derivatives of the androstane and pregnane series, as well as pharmaceutical compositions and methods for modulating brain excitability. More particularly, the invention relates to 3α-hydroxy, 17-(un)substituted derivatives of the androstane series and 21-substituted derivatives of the pregnane series. These derivatives are capable of acting at a recently identified site on the GRC, thereby modulating brain excitability in a manner that alleviates stress, anxiety, insomnia, mood disorders that are amenable to GRC-active agents (such as depression) and seizure activity.

The steroid derivatives of this invention are those having the general structural formula (I):

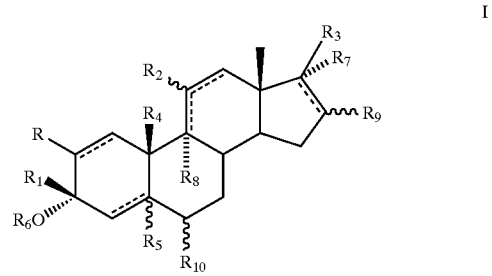

wherein R, $R_1$, $R_2$, $R_3$, $R_4$, $R_5$, $R_6$, $R_7$, $R_8$, $R_9$ and $R_{10}$ are further defined herein and the dotted lines are single or double bonds. The structure having Formula I includes androstanes, pregnanes ($R_4$=methyl), 19-norandrostanes, and norpregnanes ($R_4$=H).

The present invention also includes pharmaceutically acceptable esters and salts of the compounds of Formula I, including acid addition salts. It is believed that the 3α-hydroxyl may also be masked as a pharmaceutically acceptable ester due to the fact that the ester will be cleaved off as the prodrug is converted to drug form. These are referred to herein as cleavable esters.

The compounds of the present invention are modulators of the excitability of the central nervous system as mediated by their ability to regulate chloride ion channels associated with the GABA receptor complex. Applicants' experiments have established that these compounds have anticonvulsant, anxiolytic, and sedative hypnotic activity similar to the actions of known agents such as the BZs, but act at a distinct site on the GRC.

The relationship of endogenous metabolites of progesterone to processes associated with reproduction (estrus cycle and pregnancy) is well established (Marker, R. E. et al., *J. Am. Chem. Soc.* 59:616–618 (1937)). However, it was just recently recognized how to treat disorders by modulating brain excitability through the use of steroid metabolites and their derivatives. See, U.S. Pat. No. 5,208,227, issued May 4, 1993; U.S. Pat. No. 5,120,723, issued Jun. 9, 1992; and U.S. Pat. No. 5,232,917, issued Aug. 3, 1993.

Desirable objects of the pharmaceutical compositions and methods of this invention are the treatment of stress, anxiety, PMS, PND, and seizures such as those caused by epilepsy to ameliorate or prevent the attacks of anxiety, muscle tension, and depression common with patients suffering from these central nervous system abnormalities. An additional desirable object of the compositions and methods is to treat insomnia and produce hypnotic activity. Another desirable object of the compounds and methods is to induce anesthesia, particularly by intravenous administration. The present invention is directed to novel compounds and their use in pharmaceutical compositions and methods to treat such disorders by modulating brain excitability.

Another aspect of the present invention relates to a method of inducing sleep and maintaining substantially the level of REM sleep that is found in normal sleep, wherein substantial rebound insomnia, as defined herein, is not induced. This method comprises administering an effective amount of a compound of the invention. The compounds of the invention are able to increase NREM sleep and the total sleep period, without substantially affecting the amount of REM sleep.

BRIEF DESCRIPTION OF THE DRAWING

The present invention may be better understood and its advantages appreciated by referring to the accompanying drawing wherein.

DETAILED DESCRIPTION OF THE PREFERRED EMBODIMENTS

Figure 1:
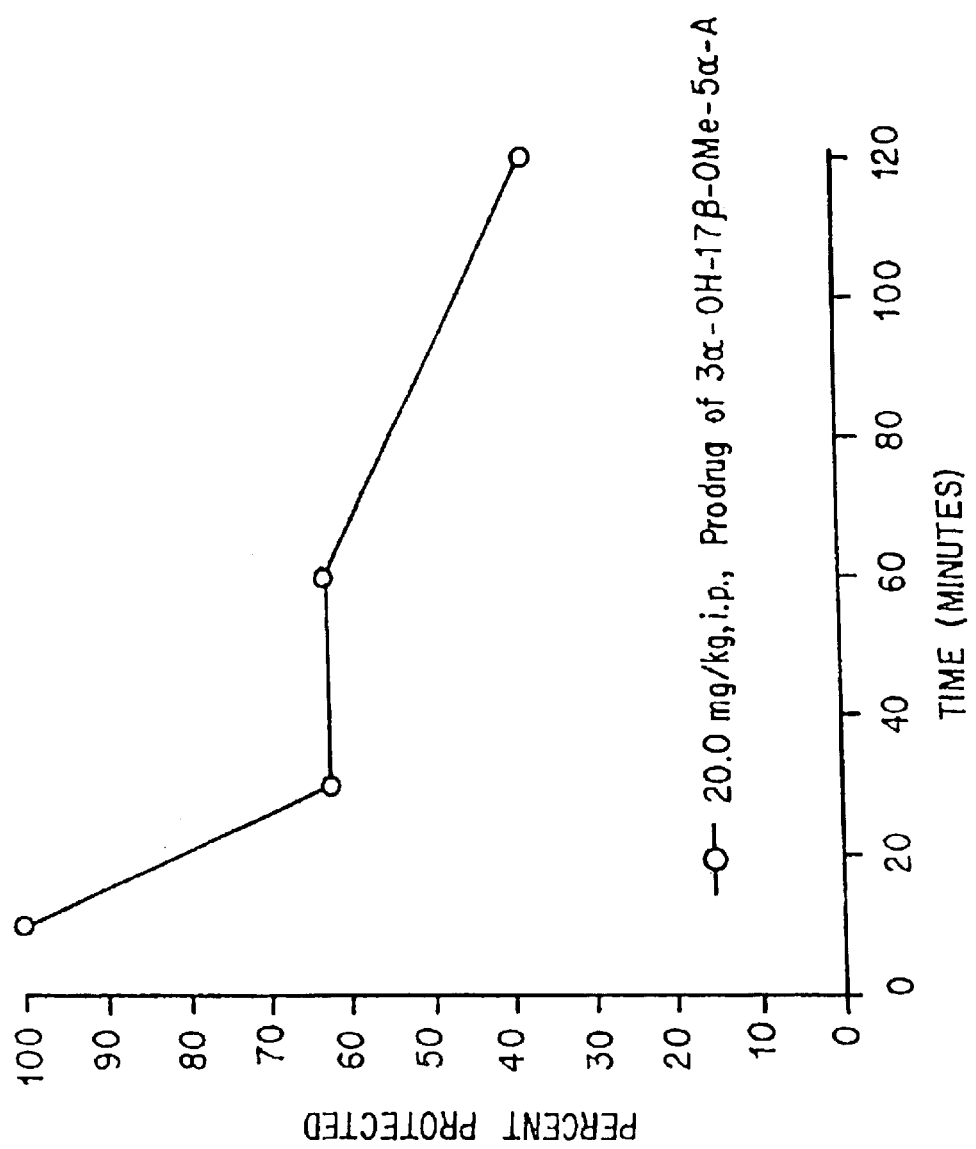
FIG. 1 is a plot of the time course of anti-metrazol activity of a prodrug of 3α-hydroxy-17β-methoxy-5α-androstane (administered i.p. at a dose of 20.0 mg/kg).

The compounds of the present invention are derivatives of various 3α-hydroxylated-pregnanes and 3α-hydroxylated-androstanes, and ester, ether, sulfonate, sulfate, phosphonate, phosphate, oxime, thiosulfate, heterocyclic and heteroaryl derivatives thereof, and derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., *Methods in Enzymology*, 112:309–323 (1985); Bodor, N., *Drugs of the Future*, 6(3):165–182 (1981); and Bundgaard, H., "Design of Prodrugs: Bioreversible-Derivatives for Various Functional Groups and Chemical Entities," in *Design of Prodrugs*, H. Bundgaard, ed., Elsevier, N.Y. (1985). It should be noted that some of the synthetic derivatives forming part of the present invention may not be true prodrugs because, in addition to the above characteristics, they also possess intrinsic activity. However, for purposes of this application they will be referred to as prodrugs.

Earlier studies (Gee, K. W. et al., *European Journal of Pharmacology*, 136:419–423 (1987)) demonstrated that certain 3α-hydroxylated steroids are orders of magnitude more potent as modulators of the GRC than others had reported (Majewska, M. D. et al., *Science* 232:1004–1007 (1986); Harrison, N. L. et al., *J. Pharmacol. Exp. Ther*. 241:346–353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (Gee, K. W. et al., *European Journal of Pharmacology*, 136:419–423 (1987); Wieland et al., *Psychopharmacology* 118(1):65–71 (1995)). Various synthetic steroids have been prepared as neuroactive steroids. See, for example, U.S. Pat. No. 5,232,917, issued Aug. 3, 1993, which discloses neuroactive steroid compounds useful in treating stress, anxiety, insomnia, seizure disorders and mood disorders that are amenable to GRC-active agents, such as depression, in a therapeutically beneficial manner. Furthermore, it has been previously demonstrated that these steroids interact at a unique site on the GRC which is distinct from other known sites of interaction (i.e., barbiturate, BZ, and GABA) where therapeutically beneficial effects on stress, anxiety, sleep, mood disorders and seizure disorders have been previously elicited (Gee, K. W. and Yamamura, H. I., "Benzodiazepines and Barbiturates: Drugs for the Treatment of Anxiety, Insomnia and Seizure Disorders," in *Central Nervous System Disorders*, D. C. Horvell, ed., Marcel-Dekker, New York (1985), pp. 123–147; Lloyd, K. G. and Morselli, P. L., "Psychopharmacology of GABAergic Drugs," in *Psychopharmacology: The Third Generation of Progress*, H. Y. Meltzer, ed., Raven Press, N. Y. (1987), pp. 183–195; and Gee, K. W. et al., *European Journal of Pharmacology*, 136:419–423 (1987). These compounds are desirable for their duration, potency and oral activity (along with other forms of administration).

Definitions

In accordance with the present invention and as used herein, the following terms, when appearing alone or as part of a moiety, are defined with the following meaning, unless explicitly stated otherwise.

The term "alkyl," as used herein at all occurrences, refers to saturated aliphatic groups including staight chain, branched chain, and cyclic groups, all of which may be optionally substituted. Preferred alkyl groups contain 1 to 10 carbon atoms. Suitable alkyl groups include methyl, ethyl and the like, and may be optionally substituted.

The term "alkenyl," as used herein at all ocurrences, refers to unsaturated groups which contain at least one carbon-carbon double bond and includes straight chain, branched chain, and cyclic groups, all of which may be optionally substituted. Preferable alkenyl groups have 2 to 10 carbon atoms.

The term "alkynyl," as used herein at all occurrences, refers to unsaturated hydrocarbon groups which contain at least one carbon-carbon triple bond and includes straight chain and branched chain groups which may be optionally substituted. Preferred alkynyl groups have two to eighteen carbon atoms. More preferred alkynyl groups have two to twelve carbon atoms. Most preferred alkynyl groups have two to seven carbon atoms. Suitable alkynyl groups include ethynyl, propynyl, butynyl, pentynyl, and the like which may be optionally substituted with cyano, acetoxy, halo, hydroxy or keto.

The term "alkoxy" refers to the ether —O-alkyl, wherein alkyl is defined as above.

The term "aryloxy" refers to the ether —O-aryl wherein aryl is defined herein below.

The term "aryl" refers to aromatic groups which have at least one ring having a conjugated pi electron system and includes carbocyclic aryl and biaryl, both of which may be optionally substituted. Preferred aryl groups have 6 to 10 carbon atoms. Suitable aryl groups include phenyl and naphthyl.

The term "cabocyclic aryl" refers to groups wherein the ring atoms on the aromatic ring are carbon atoms. Carbocyclic aryl groups include phenyl and naphthyl groups, which groups are optionally substituted. Substituted phenyl has preferably one to three, four or five substituents, such being advantageously, lower alkyl, amino, aminocarbonyl cyano, carboxylate ester, hydroxy, lower alkoxy, halogen, lower acyl, and nitro.

The term "aralkyl" refers to an alkyl group substituted with an aryl group. Suitable aralkyl groups include benzyl, and the like, and may be optionally substituted.

The term "alkanoyloxy" refers to —O—C(O)$R^a$, wherein $R^a$ is alkyl, alkenyl, alkynyl, aryl or aralkyl.

The term "carbalkoxy" refers to —C(O)O$R^b$, wherein $R^b$ is alkyl, alkenyl, alkynyl, aryl or aralkyl.

The term "carboxamido" refers to —C(O)N$R^c R^d$, wherein $R^c$ and $R^d$ are independently selected from hydrogen, alkyl, alkenyl, alkynyl, aryl or aralkyl.

The term "acyl" refers to the alkanoyl group —C(O)R$^g$ where R$^g$ is alkyl, alkenyl, alkynyl, aryl, or aralkyl.

The term "amino" refers to —NR$^h$R$^i$, where R$^h$ and R$^i$ are independently hydrogen or lower alkyl or are joined together (with the nitrogen atom to which they are attached) to give a 5 or 6-membered ring, e.g. pyrrolidine, morpholino or piperidine rings. The term "dialkylamino" refers to —NR$^e$R$^f$ where R$^e$ and R$^f$ are independently lower alkyl groups or together with the nitrogen atom to which they are attached, form the rest of a morpholino group. Suitable dialkylamino groups include dimethylamino, diethylamino, and morpholino.

The term "thio" refers to —SR$^m$, where R$^m$ is hydrogen, alkyl, alkenyl, alkynyl, aryl or aryl(lower)alkyl.

The term "sulfinyl" refers to —SO$_2$R$^n$, where R$^n$ is alkyl alkenyl, alkynyl, aryl or aryl(lower)alkyl.

The term "sulfonyl" refers to —SO$_2$R$^o$, where R$^o$ is hydrogen, alkyl, alkenyl, alkynyl, aryl or aryl(lower)alkyl.

The term "sulfonamido" refers to —SO$_2$NR$^k$R$^l$, wherein R$^k$ and R$^l$ are independently hydrogen or lower alkyl.

The term "optionally substituted" or "substituted," unless otherwise specifically defined herein, refers to groups substituted by one to five substituents, independently selected from lower alkyl (acyclic and cyclic), aryl (carboaryl and heteroaryl), alkenyl, alkynyl, alkoxy, halo, haloalkyl (including trihaloalkyl, e.g. trifluoromethyl), amino, mercapto, alkylthio, alkylsulfinyl, alkylsulfonyl, nitro, alkanoyl, alkanoyloxy, alkanoyloxyalkanoyl, alkoxycarboxy, carbalkoxy (—COOR$^j$, wherein R$^j$ is lower alkyl), carboxamido (—CONR$^k$R$^l$, wherein R$^k$ and R$^l$ are defined as above), formyl, carboxy, hydroxy, cyano, azido, keto and cyclic ketals thereof, alkanoylamido, heteroaryloxy, heterocarbocyclicoxy and hemisuccinate ester salts.

The term "lower" is referred to herein in connection with organic radicals or compounds defines one up to and including ten, preferably up to and including six, and advantageously one to four carbon atoms. Such groups may be straight chain, branched chain, or cyclic.

The term "heterocyclic" refers to carbon containing radicals having three, four, five, six, or seven membered rings and one or two O, N or S heteroatoms, e.g., thiazolidine, tetrahydrofuran, 1,4-dioxane, 1,3,5-trioxane, pyrrolidine, piperidine, quinuclidine, dithiane, tetrahydropyran, ∈-caprolactone, ∈-caprolactam, ω-thiocaprolactam, and morpholine.

The term "heteroarl" refers to carbon containing 5–14 membered cyclic unsaturated radicals containing one, two, three or four O, N or S atoms and having 6, 10 or 14 π electrons delocalized in one or more rings, e.g., pyridine, oxazole, indole, purine, pyrimidine, imidazole, benzimidazole, indazole, 2H-1,2,4-triazole, 1,2,3-triazole, 2H-1,2,3,4-terazole, 1H-1,2,3,4-tetrazole, benzotriazole, 1,2,3-triazolo[4,5-β]pyridine, thiazole, isoxazole, pyrazole, quinoline, cytosine, thymine, uracil, adenine, guanine, pyrazine, picolinic acid, picoline, furoic acid, furfural, furyl alcohol, carbazole, 9H-pyrido[3,4-β]indole, isoquinoline, pyrrole, thiophene, furan, 9(10H)-acridone, phenoxazine, and phenothiazine, each of which may be optionally substituted as discussed above.

The term "quaternary ammonium salt" refers to quaternary ammonium salts of amino compounds and heteroaryl compounds described above, formed by reaction of the amino compound or the heteroaryl compound with an electrophilic reagent such as an alkyl, alkenyl, alkynyl, cycloalkylalkyl, aralkyl or aralkynyl, halide, tosylate, sulfate, mesylate or the like. Specific examples of electrophilic reagents include methyl iodide, ethyl iodide, n-butyl iodide and phenethyl iodide.

The term "EDA" refers to ethylenediamine.

The term "pharmaceutically acceptable esters or salts" refers to ester or salts of Formula I derived from the combination of a compound of this invention and an organic or inorganic acid, or base. Basic salts are formed by mixing a solution of a particular compound of the present invention with a solution of a pharmaceutically acceptable non-toxic base, such as, sodium hydroxide, potassium hydroxide, sodium bicarbonate, sodium carbonate, or an amino compound, such as, choline hydroxide, Tris, bis-Tris, N-methylglucamine, arginine, and the like. Acid salts are formed mixing a solution of a particular compound of the present invention with a solution of a pharmaceutically acceptable non-toxic organic acid or dioic acid, such as acetic, propionic, maleic, fumaric, ascorbic, pimelic, succinic, glutaric, bismethylene-salicylic, methanesulfonic, ethane-disulfonic, oxalic, tartaric, salicylic, citric, gluconic, itaconic, glycolic, p-aminobenzoic, aspartic, glutamic, gamma-amino-butyric, α-(2-hydroxyethylamino)propionic, glycine and other α-amino acids, phosphoric, sulfuric, glucuronic, and 1-methyl-1,4-dihydronicotinic. Esters are formed from steroidal alcohols and a suitably activated acid. Esters are further discussed herein.

The term "dioic acids" refers to $C_{1-5}$ alkylene groups substituted with two carboxy groups, for example, malonic acid, succinic acid, glutaric acid, adipic acid, pimelic acid, and suberic acid. Hemi-ester salts of the dioic acids include the sodium, lithium, potassium, magnesium and calcium salts thereof.

According to the present invention, ketals include diethers of lower alkanols, e.g. dimethyl and diethyl ketals, as well as cyclic ketals which include diethers of $C_{2-3}$ alkanediols, which may be optionally substituted, e.g., ethylene ketals and propylene ketals.

Embodiment 1a

In its broadest aspects, the present invention is directed to steroid derivatives having the general Formula I:

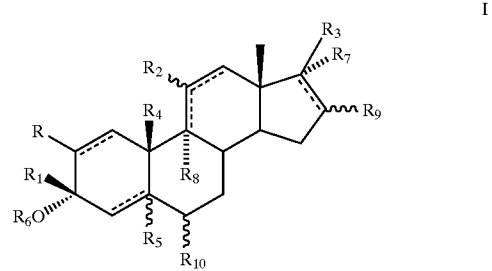

wherein
R is one of hydrogen, amino, thio, sulfinyl, sulfonyl, halogen, lower alkoxy, alkyl, substituted alkyl, alkenyl, alkynyl or substituted alkynyl;
$R_1$ is one of hydrogen, alkyl, alkenyl, alkynyl, haloalkyl, dihaloalkyl, trihaloalkyl, optionally substituted aralkynyl, alkoxyalkyl, aminoalkyl, cyano, cyanoalkyl, thiocyanoalkyl, azidoalkyl, optionally substituted arylalkyl, arylalkenyl, optionally substituted aryl, optionally substituted aralkylalkynyl, alkanoyloxyalkynyl, optionally substituted heteroaryloxyalkynyl, oxoalkynyl or a ketal thereof, cyanoalkynyl, optionally substituted heteroarylalkynyl, hydroxyalknyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_2$ is one of hydrogen, hydroxy, alkoxy, alkanoyloxy, carbalkoxy, a keto group or amino group;

$R_3$ is one of hydrogen, alkoxy, substituted alkoxy, alkenyloxy, aminocarbonyl, monoalkylaminocarbonyl, dialkylaminocarbonyl, sulfinyl, sulfonyl, thio, sulfonamido, alkynyloxy, optionally substituted aryloxy, optionally substituted arylalkyloxy, an optionally substituted 1,3-dioxolan-4-one of an acetyl group, an optionally substituted 1,3-dioxan-4-one of an acetyl group, an optionally substituted 1,3-oxathiolan-5-one of an acetyl group, an optionally substituted 1,3-oxathioan-5-one of an acetyl group, —O—C(O)—NR'R", —C(O)—CH$_2$—Y—G, —C(O)—CH$_2$—O—D —C(O)—CH$_2$—O—E, —C(O)—CH$_2$—Z—G, —C(O)—CH$_2$—Y'—Z—G, or —C(O)—CH$_2$—Y'—Z—A, wherein R' and R" independently represent hydrogen or optionally substituted alkyl, or taken together with the nitrogen to which they are attached form a 3- to 6-membered heterocyclic ring;

Y is one of S, SO or SO$_2$;

Y' is one of O, S, SO or SO$_2$;

Z is one of alkyl, alkenyl or alkynyl;

G is one of C-attached heteroaryl, optionally substituted aryl, a quaternary ammonium salt of a nitrogen containing heteroaryl group or a quaternary salt of an amino substituted aryl group;

D is C-attached heteroaryl or a quaternary ammonium salt of a nitrogen containing heteroaryl group;

E is optionally substituted aryl or a quaternary ammonium salt of an amino substituted aryl group;

A is one of amino, amido, cyano, thiocyano, azido, nitro, hydroxy, halo, carboxyl, alkoxy, alkoxycarbonyl, alkanoyloxy, hydrogen, sulfate, thiosulfate, sulfonate, alkylthio, alkylsulfinyl, alkylsulfonyl or mercapto;

$R_4$ is one of hydrogen or lower alkyl, $R_5$ is hydrogen, or when a double bond is present between C4 and C5 of the steroid ring system, then $R_5$ is not present;

$R_6$ is one of hydrogen, alkanoyl, aminocarbonyl or alkoxycarbonyl;

$R_7$ is one of hydrogen, halogen, hydroxy, alkoxy, alkanoyloxy or carbalkoxy;

$R_8$ is one of hydrogen or halogen;

$R_9$ is one of hydrogen, halogen, alkyl, alkoxy, arylalkoxy or amino;

$R_{10}$ is one of hydrogen, halogen, alkyl, haloalkyl, hydroxy, alkoxy, alkanoyloxy, carbalkoxyl, cyano, thiocyano or mercapto; and the dotted lines indicate that a single or double bond may be present;

provided that:

when $R_3$ is $C_{1-3}$ alkoxy or $C_{1-6}$ alkenyloxy and R is hydrogen or α-methyl, then $R_1$ is other than hydrogen; or when $R_3$ is $C_{1-4}$alkoxy($C_{1-4}$)alkoxy, then $R_1$ is other than hydrogen or 1-propynyl; or when $R_3$ is hydrogen and $R_2$ is hydrogen, hydroxy, a keto group or an amino group, then $R_1$ is not hydrogen, alkyl or cyanoalkyl; or when $R_3$ is aminocarbonyl, monoalkylaminocarbonyl, dialkylaminocarbonyl, then $R_1$ is not hydrogen or alkyl; or when $R_3$ is —C(O)—CH$_2$—Y—G, and G is C-attached heteroaryl or optionally substituted aryl, then $R_1$ is other than hydrogen or alkyl; or when $R_3$ is —C(O)—CH$_2$—O—E, and E is optionally substituted aryl, then $R_1$ is other than hydrogen; or when $R_3$ is —C(O)—CH$_2$—Y'—Z—G, and Y' is O, and G is aryl, then $R_1$ is other than hydrogen; or when $R_3$ is —C(O)—CH$_2$—Y'—Z—G, and Y' is S, SO, or SO$_2$, and G is aryl, then $R_1$ is other than hydrogen or alkyl; or when $R_3$ is —C(O)—CH$_2$—Z—G, then $R_1$ is other than hydrogen; or when $R_3$ is —C(O)—CH$_2$—Y'—Z—A, and Y' is O, and A is hydrogen, halo, carboxyl, alkoxycarbonyl, alkoxy, cyano or amino, then $R_1$ is other than hydrogen; or when $R_3$ is —C(O)—CH$_2$—Y'—Z—A, and Y' is S, SO, or SO$_2$, and A is hydrogen, halo, carboxyl, alkoxycarbonyl, or amino, then $R_1$ is other than hydrogen or alkyl.

The present invention also includes pharmaceutically acceptable esters and salts of the compounds of Formula I, including acid addition salts. It is believed that the 3α-hydroxyl may also be masked as a pharmaceutically acceptable ester due to the fact that the ester will be cleaved off as the prodrug is converted to drug form. These are referred to herein as cleavable esters.

Embodiment 1b

One group of useful compounds encompassed by the broad aspect of the present invention includes compounds of Formula I, wherein:

the bond between C4 and C5 of the steroid ring system is a single bond;

R is one of hydrogen, halogen, lower alkoxy, alkyl, substituted alkyl, alkynyl or substituted alkynyl;

$R_1$, $R_2$, $R_4$, $R_6$, $R_7$, $R_8$, $R_9$ and $R_{10}$ are defined as above;

$R_3$ is one of hydrogen, alkoxy, substituted alkoxy, alkenyloxy, alkynyloxy, optionally substituted aryloxy, optionally substituted arylalkyloxy, —O—C(O)—NR'R", —C(O)—CH$_2$—Y—G, —C(O)—CH$_2$—O—D —C(O)—CH$_2$—O—E, —C(O)—CH$_2$—Y'—Z—G, or —C(O)—CH$_2$—Y'—Z—A, wherein R' and R" independently represent hydrogen or optionally substituted alkyl, or taken together with the nitrogen to which they are attached form a 5- or 6-membered heterocyclic ring;

Y, Y', Z, G, D, E, and A are defined as above;

$R_5$ is hydrogen; and wherein all of the relevant provisos that are recited above for Embodiment 1a are applicable to this subgenus of compounds.

Embodiments 1a' and 1b'

In preferred aspects of Embodiments 1a and 1b the steroid derivatives have the general Formula I, wherein R, $R_1$, $R_2$, $R_3$, R', R", Y, Y', Z, G, D, E, A, $R_4$, $R_5$, $R_6$, $R_7$, $R_8$, $R_9$ and $R_{10}$ are defined as above for Embodiments 1a or 1b. However, the following provisos apply to each of the earlier embodiments:

when $R_3$ is $C_{1-6}$ alkoxy or $C_{1-6}$ alkenyloxy, then $R_1$ is other than hydrogen or methyl; or when $R_3$ is hydrogen and $R_2$ is hydrogen, hydroxy, a keto or an amino group, then $R_1$ is not hydrogen, alkyl or cyanoalkyl; or when $R_3$ is —C(O)—CH$_2$—Y—G, and G is C-attached heteroaryl or optionally substituted aryl, then $R_1$ is other than hydrogen or alkyl; or when $R_3$ is —C(O)—CH$_2$—Z—G, then $R_1$ is other than hydrogen or alkyl; or when $R_3$ is —C(O)—CH$_2$—O—E, and E is optionally substituted aryl, then $R_1$ is other than hydrogen or methyl; or when $R_3$ is —C(O)—CH$_2$—Y'—Z—G, and G is optionally substituted aryl, then $R_1$ is other than hydrogen or alkyl; or when $R_3$ is —C(O)—CH$_2$—Y'—Z—A, and A is hydrogen, halo, carboxyl, alkoxycarbonyl, alkoxy, cyano or amino, then $R_1$ is other than hydrogen or alkyl.

Preferred Values for All Embodiments of the Invention

Each of the following groups of preferred values applies to all embodiments of the present invention, unless otherwise specifically provided for. Preferred compounds of Formula I include compounds wherein R is hydrogen or lower alkoxy, with hydrogen being more preferred; $R_3$ is defined as above, and is preferably one of the groups described hereinbelow; $R_5$, $R_6$, $R_7$, $R_8$, $R_9$ and $R_{10}$ are hydrogen; and $R_1$ is substituted arylalkynyl, e.g. $R_1$ is 4-substituted phenylalkynyl such as 4-acetylphenylethynyl, 4-methoxyphenylethynyl, 4-N,N-dimethylaminophenylethynyl, 4-cyanophenylethynyl, 4-carboxyphenylethynyl ethyl ester, 4-N,N-dialkylamidophenylethynyl, or wherein $R_1$ is oxoalkynyl, hydroxyalkynyl, acetoxyalkynyl, cyanoalkynyl, or alkoxyalkynyl.

Additional preferred compounds are compounds of Formula I wherein R is hydrogen, halo, lower alkoxy, alkynyl or substituted alkynyl; $R_1$ is substituted arylethynyl; $R_2$ is hydrogen, a keto group or a dimethylamino group; $R_4$ is hydrogen or methyl; $R_5$, $R_6$, $R_7$, $R_8$, $R_9$ and $R_{10}$ are each hydrogen; and the dotted lines all represent single bonds.

Further preferred compounds are compounds of Formula I that are esters of hydroxyl groups at the 3-position. Preferred esters are those obtained from their corresponding acids and dioic acids: acetic, propionic, maleic, fumaric, ascorbic, pimelic, succinic, glutaric, bismethylene-salicylic, methanesulfonic, ethane-di-sulfonic, oxalic, tartaric, salicylic, citric, gluconic, itaconic, glycolic, p-aminobenzoic, aspartic, glutamic, gamma-amino-butyric, α-(2-hydroxyethylamino)propionic, glycine and other α-amino acids, phosphoric, sulfuric, glucuronic, and 1-methyl-1,4-dihydronicotinic.

17-Ether Derivatives of 3α-Hydroxy Androstanes

A first sub-genus of compounds according to the present invention includes 17-ether derivatives of 3α-hydroxy androstanes. Steroid derivatives of this aspect of the present invention include those having the structural Formula I, as shown above, wherein:

R, $R_1$, $R_2$, $R_4$, $R_5$, $R_6$, $R_7$, $R_8$, $R_9$ and $R_{10}$ are as defined above for Embodiment 1a; and $R_3$ is one of alkoxy, substituted alkoxy, alkenyloxy, alkynyloxy, optionally substituted aryloxy, optionally substituted arylalkyloxy or —OC(O)NR'R", wherein R' and R" independently represent hydrogen, optionally substituted alkyl, or taken together form a 5- or 6-membered heterocyclic ring;

provided that:

when $R_3$ is $C_{1-6}$ alkoxy or $C_{1-6}$ alkenyloxy and R is hydrogen or α-methyl, then $R_1$ is other than hydrogen; and when $R_3$ is $C_{1-4}$alkoxy($C_{1-4}$)alkoxy, then $R_1$ is other than hydrogen or 1-propynyl.

Preferred values in this aspect of the present invention include those values indicated above as generally preferred, and also the following:

$R_3$ is alkoxy, such as methoxy, ethoxy or propoxy, or substituted alkoxy, such as —OCH$_2$CH$_2$OH, —OCH$_2$C≡CH or OCH$_2$C≡C-PhCOMe;

$R_4$ is hydrogen or lower alkyl, more preferably hydrogen or methyl;

$R_5$, $R_6$, $R_7$, $R_8$, $R_9$ and $R_{10}$ are preferably each hydrogen; and the dotted lines all represent single bonds.

Preferred compounds according to this aspect of the present invention include: 3α-hydroxy-3β-phenylethynyl-17β-methoxy-5β-androstane; 3α-hydroxy-3β-phenylethynyl-17β-methoxy-5α-androstane; 3α-hydroxy-3β-(3',4'-dimethoxyphenyl)ethynyl-17β-methoxy-5β-androstane; 3α-hydroxy-3β-(4'-methylphenyl)ethynyl-17β-methoxy-5β-androstane; 3α-hydroxy-3β-(2'-methoxyphenyl)ethynyl-17β-methoxy-5β-androstane; 3α-hydroxy-3β-(4'-carboxyphenyl)ethynyl-17β-methoxy-5β-androstane ethyl ester; 3α-hydroxy-3β-(4'-acetoxyacetylphenyl)ethynyl-17β-methoxy-5β-androstane; 3β-(4'-acetylphenyl)ethynyl-3α-hydroxy-17β-methoxy-5α-androstane; 3β-(4'-acetylphenyl)ethynyl-3α-hydroxy-17β-methoxy-5β-androstane; 3β-(4'-dimethylamiophenyl)ethynyl-3α-hydroxy-17β-methoxy-5β-androstane; 3β-(4'-biphenyl)ethynyl-3α-hydroxy-17β-methoxy-5β-androstane; 3α-hydroxy-3β-(4'-nitrophenyl)ethynyl-17β-methoxy-5β-androstane; 3α-hydroxy-3β-(4'-methoxyphenyl)ethynyl-17β-methoxy-5β-androstane; 3β-(4'-trifluoromethylphenyl)ethynyl-3α-hydroxy-17β-methoxy-5β-androstane; 3β-(4'-chlorophenyl)ethynyl-3α-hydroxy-17βmethoxy-5β-androstane; 3β-(4'-cyanophenyl)ethynyl-3α-hydroxy-17β-methoxy-5β-androstane; 3β-(4'(R/S)-hydroxypentynyl)-3α-hydroxy-17β-methoxy-5β-androstane; 3α-hydroxy-3β-phenyl-17β-methoxy-5β-androstane; 3α-hydroxy-3β-benzyl-17β-methoxy-5β-androstane; 3α-hydroxy-3β-(2'-phenylethyl)-17β-methoxy-5β-androstane; 3α-hydroxy-3β-[2-(3',4'-dimethoxyphenyl)ethyl]-17β-methoxy-5β-androstane; 3α-hydroxy-3β-[6'-oxo-1'-heptynyl]-17β-methoxy-5β-adrostane; 3α-hydroxy-3β-(7'-oxo-1'-octynyl)-17β-methoxy-5β-androstane; 3α-hydroxy-3β-(4'-oxo-1'-pentynyl)-17β-methoxy-5β-androstane; 3β-[5'-(R/S)-hydroxyhexynyl]-3α-hydroxy-17β-methoxy-5β-androstane; 3β-(4'-hydroxybutynyl)-3α-hydroxy-17β-methoxy-5β-androstane; 3β-(4'-hydroxybutynyl)-3α-hydroxy-17β-methoxy-5α-androstane; 3β-(4'-acetoxyphenylethynyl)-3α-hydroxy-17β-methoxy-5β-androstane; 3β-(4'-acetylphenylethynyl)-3α-hydroxy-19-nor-17β-methoxy-5β-androstane; 3β-(4'-carboxyphenylethynyl)-3α-hydroxy-19-nor-17β-methoxy-5β-androstane ethyl ester; 3β-(4'-carboxyphenylethynyl)-3α-hydroxy-17βmethoxy-5α-androstane ethyl ester; 3β-[4'-(N,N-diethylcarboxamido)phenyl]ethynyl-3α-hydroxy-17β-methoxy-5β-androstane; 3α-hydroxy-3β-[5-oxo-1-hexynyl]-17β-methoxy-5β-androstane; 3α-hydroxy-3β-[5'-oxo-1'-hexynyl]-17β-methoxy-5β-androstane cyclic 5'-(1,2-ethanediyl acetal); 3β-(5-cyano-1-pentynyl)-3α-hydroxy- 17β-methoxy-5β-androstane; 3α-hydroxy-3β-(2-pyridyl) ethynyl-17β-methoxy-5β-androstane; 3β-(6-hydroxy-1-hexynyl)-3α-hydroxy-17β-methoxy-5β-androstane; 3β-(6'-hydroxy-1'-hexynyl)-3α-hydroxy-17β-methoxy-5β-androstane 6'-hemisuccinate sodium salt; 3β-(5'-hydroxy-1'-pentynyl)-3α-hydroxy-17β-methoxy-5β-androstane; 3β-(5'-hydroxy-1'-pentynyl)-3α-hydroxy-17β-methoxy-5β-androstane 5'-hemisuccinate sodium salt; 3β-(4'-hydroxy-1'-butynyl)-3α-hydroxy-17β-methoxy-5β-androstane 4'-hemisuccinate sodium salt; 3β-(4'-cyano-1'-butynyl)-3α-hydroxy-17β-methoxy-5β-androstane; 3β-(5'-acetoxy-1'-pentynyl)-3α-hydroxy-17β-methoxy-5β-androstane; 3β-(4'-acetoxy-1'-butynyl)-3α-hydroxy-17β-methoxy-5β-androstane; 3β-(4'-acetoxy-1'-butynyl)-3α-hydroxy-17β-methoxy-5α-androstane; 3β-(6'-acetoxy-1'-hexynyl)-3α-hydroxy-17β-methoxy-5β-androstane; 3α-hydroxy-3β-[3-(2'-propynyloxy)-1-propynyl]-17β-methoxy-5β-androstane; 3α-hydroxy-3β-(3-methoxy-1-propynyl)-17β-methoxy-5β-androstane; 3α-hydroxy-3β-(3-methoxy-1-propynyl)-17β-methoxy-5α-androstane; 3α-hydroxy-3β-[3-(4'-pyridinyloxy)-1-propynyl]-17β-methoxy-5β-androstane; 3α-hydroxy-3β-[3-(1'H-1,2,3-triazol-1'-yl)-1-propynyl]-17β-methoxy-5β-androstane; 3α-hydroxy-3β-[3-(2'H-1,2,3-triazol-2'-yl)-1-propynyl]-17β-methoxy-5β-androstane; 3α-hydroxy-3β-(2'-thienyl)ethynyl-17β-methoxy-5β-androstane; 3α-hydroxy-3β-(3'-phenyl-1'-propynyl)-17β-methoxy-5β-androstane; 3α-hydroxy-3β-(3'-phenylpropyl)-17β-methoxy-5β-androstane; 3α-hydroxy-3β-[3-(1'H-pyrazol-1'-yl)-1-propynyl]-17β-methoxy-5β-androstane; 3β-(3'-acetylphenylethynyl)-3α-hydroxy-17β-methoxy-5β-androstane; and 3β-(3'-acetoxy-3'-propynyl)-3α-hydroxy-17β-methoxy-5β-androstane.

The more preferred neuroactive steroids according to this aspect of the present invention include 3β-(4'-acetylphenyl) ethynyl-3α-hydroxy-17β-methoxy-5α-androstane; 3β-(4'-carboxylphenyl)ethynyl-3α-hydroxy-17β-methoxy-5α-androstane ethyl ester; 3β-(4'-acetylphenyl)ethynyl-3α-hydroxy-17β-methoxy-5β-androstane; 3β-(4'-carboxylphenyl)ethynyl-3α-hydroxy-17β-methoxy-5β-androstane ethyl ester; 3β-(4'-acetylphenyl)ethynyl-3α-hydroxy-17β-methoxy-5β-19-norandrostane; 3β-(4'-carboxylphenyl)ethynyl-3α-hydroxy-17β-methoxy-5β-19-norandrostane ethyl ester; 3β-(4'-dimethylaminophenyl) ethynyl-17β-methoxy-5β-androstane; 3β-(4'-biphenyl) ethynyl-3α-hydroxy-17β-methoxy-5β-androstane; 3α-hydroxy-3β-(4'-methoxyphenyl)ethynyl-17β-methoxy-5β-androstane; 3β-(4'-trifluoromethylphenyl)ethynyl-3α-hydroxy-17β-methoxy-5β-androstane; 3β-(4'-chlorophenyl) ethynyl-3α-hydroxy-17β-methoxy-5β-androstane; 3β-[4' (R/S)-hydroxypentynyl]-3α-hydroxy-17β-methoxy-5β-androstane; 3β-(4'-hydroxybutynyl)-3α-hydroxy-17β-methoxy-5β-androstane; 3β-(4'-hydroxybutynyl)-3α-hydroxy-17β-methoxy-5α-androstane; and 3α-hydroxy-3β-[3-(2'H-1,2,3-triazol-2'-yl)-1-propynyl]-17β-methoxy-5β-androstane.

The especially preferred neuroactive steroids according to this aspect of the present invention include 3β-(4'-acetylphenyl)ethynyl-3α-hydroxy-17β-methoxy-5α-androstane; 3β-(4'-acetylphenyl)ethynyl-3α-hydroxy-17β-methoxy-5β-androstane; 3β-(4'-carboxylphenyl)ethynyl-3α-hydroxy-17β-methoxy-5α-androstane ethyl ester; 3β-(4'-carboxyphenyl)ethynyl-3α-hydroxy-17β-methoxy-5β-androstane ethyl ester; 3β-(4'-dimethylaminophenyl) ethynyl-17β-methoxy-5β-androstane; 3β-(4'-biphenyl) ethynyl-3α-hydroxy-17β-methoxy-5β-androstane; 3β-(4'-hydroxybutynyl)-3α-hydroxy-17β-methoxy-5β-androstane; 3β-(4'-hydroxybutynyl)-3α-hydroxy-17β-methoxy-5α-androstane; 3α-hydroxy-3β-[3-(2'H-1,2,3-triazol-2'-yl)-1-propynyl]-17β-methoxy-5β-androstane; 3β-(4'-acetylphenyl)ethynyl-3α-hydroxy-17β-methoxy-5β-19-norandrostane; and 3β-[4'(R/S)-hydroxypentynyl]-3α-hydroxy-17β-methoxy-5β-androstane.

3α-Hydroxy Androstane Derivatives

A second preferred sub-genus of compounds according to the present invention includes 3α-hydroxy androstane derivatives that are unsubstituted at the 17β-position of the steroid ring system, i.e., $R_3$ is hydrogen. Steroid derivatives of this aspect of the present invention include those having the structural Formula I, as shown above, wherein $R_3$ is hydrogen; and R, $R_1$, $R_2$, $R_4$, $R_5$, $R_6$, $R_7$, $R_8$, $R_9$ and $R_{10}$ are as defined above for Embodiment 1a;

provided that $R_1$ is not hydrogen, alkyl or cyanoalkyl.

Preferred values for R, $R_1$, $R_2$, $R_4$, $R_5$, $R_6$, $R_7$, $R_8$, $R_9$ and $R_{10}$ are those values listed as preferred for all embodiments of the invention, above.

21-Substituted 3α-Hydroxy Pregnane Derivatives

A third category of useful compounds according to the present invention includes 3α-hydroxy pregnane derivatives that have a 21-ether or 21-thioether linked, or 21-alkyl, 21-alkenyl or 21-alkynyl linked substituents. Compounds that may be used in this aspect of the present invention include those having the structural Formula I, shown above, wherein:

R, $R_1$, $R_2$, $R_4$, $R_5$, $R_6$, $R_7$, $R_8$, $R_9$ and $R_{10}$ are as defined above for Formula I;

$R_3$ is one of —C(O)—CH$_2$—Y—G, —C(O)—CH$_2$—O—D, —C(O)—CH$_2$—O—E, —C(O)—CH$_2$—Y'—Z—G or —C(O)—CH$_2$—Y'—Z—A;

Y is one of S, SO or SO$_2$;

Y' is one of O, S, SO or SO$_2$;

Z is one of alkyl, alkenyl or alkynyl;

G is one of C-attached heteroaryl, optionally substituted aryl, a quaternary ammonium salt of a nitrogen containing heteroaryl group or a quaternary ammonium salt of an amino substituted aryl group;

D is C-attached heteroaryl or a quaternary ammonium salt of a nitrogen containing heteroaryl group;

E is optionally substituted aryl or a quaternary ammonium salt of an amino substituted aryl group;

A is one of amino, amido, cyano, thiocyano, azido, nitro, hydroxy, halo, carboxyl, alkoxy, alkoxycarbonyl, alkanoyloxy, hydrogen, sulfate, thiosulfate, sulfonate, alkylthio, alkylsulfinyl, alkylsulfonyl or mercapto;

provided that:

when $R_3$ is —C(O)—CH$_2$—Y—G, and G is C-attached heteroaryl or optionally substituted aryl, then $R_1$ is other than hydrogen or alkyl; or when $R_3$ is —C(O)—CH$_2$—O—E, then $R_1$ is other than hydrogen; or when $R_3$ is —C(O)—CH$_2$—Y'—Z—G, and Y' is O, and G is aryl, then $R_1$ is other than hydrogen; or when $R_3$ is —C(O)—CH$_2$—Y'—Z—G, and Y' is S, SO, or SO$_2$, and G is aryl, then $R_1$ is other than hydrogen or alkyl; or when $R_3$ is —C(O)—CH$_2$—Y'—Z—A, and Y' is O, and A is hydrogen, halo, carboxyl, alkoxycarbonyl, alkoxy, cyano or amino, then $R_1$ is other than hydrogen; or when $R_3$ is —C(O)—CH$_2$—Y'—Z—A, and Y' is S, SO, or SO$_2$, and A is hydrogen, halo, carboxyl, alkoxycarbonyl, or amino, then $R_1$ is other than hydrogen or alkyl.

Alternatively, $R_3$ may also be —C(O)—CH$_2$—Z—G; wherein Z and G are defined directly above, with the proviso that when $R_3$ is —C(O)—CH$_2$—Z—G, then $R_1$ is other than hydrogen.

When D or G are C-attached heteroaryl, preferred heteroaryl moieties include pyridyl, pyrimidinyl, pyrazinyl, imidazolyl, triazolyl, tetrazolyl, quinolinyl, indolyl, benzimidazolyl, and isoquinolinyl.

When E or G are substituted aryl, preferred groups include phenyl, substituted by one, two, or three, most preferably one, of nitro, amino, dimethylamino, carboxy, methyl, hydroxy, methoxy, fluoro, chloro, bromo, cyano or pyrrolidinyl.

Examples of suitable values of substituents that may be used at position $R_3$ in this aspect of the invention include —COCH$_2$S-(4-PhNH$_2$), —COCH$_2$O-(4-PhN$^+$Me$_3$)I$^-$, —COCH$_2$O-4-pyridyl, —COCH$_2$O-3-pyridyl, —COCH$_2$S-(4-pyridyl) N-methyl iodide, —COCH$_2$SCH$_2$CH$_2$OH, —COCH$_2$OCH$_2$CH$_2$OH, —COCH$_2$SCH$_2$CH$_2$CH$_2$OH, —COCH$_2$SOCH$_2$CH$_2$CH$_2$OH, —COCH$_2$SO$_2$CH$_2$CH$_2$OH, —COCH$_2$SCH$_2$COO$^-$Na$^+$, —COCH$_2$SCH$_2$CH$_2$COO$^-$Na$^+$, —COCH$_2$SCH$_2$CH$_2$OSO$_3^-$TMA$^+$ (TMA is an abbreviation for trimethylammonium), —COCH$_2$SCH$_2$CH$_2$CH$_2$OSO$_3^-$Na$^+$, —COCH$_2$SCH$_2$CH$_2$SO$_3^-$Na$^+$, —COCH$_2$SCH$_2$CH$_2$CH$_2$SO$_3^-$Na$^+$, —COCH$_2$SO$_2$CH$_2$CH$_2$CH$_2$SO$_3^-$Na$^+$ and —COCH$_2$OCH$_2$CH$_2$CH$_2$SO$_3^-$Na$^+$.

Additional suitable values include —COCH$_2$O-(4-fluorophenyl), —COCH$_2$O-(6-quinolinyl), —COCH$_2$SO$_2$-(4-fluorophenyl), —COCH$_2$SO$_2$-(4-pyrrolidinophenyl), —COCH$_2$CH$_2$-(4-pyridyl), —COCH$_2$O-(4-nitrophenyl), —COCH$_2$O-(4-dimethylaminophenyl), —COCH$_2$SO-(4-nitrophenyl) and —COCH$_2$SO$_2$-(4-nitrophenyl).

Preferred compounds according to this aspect of the present invention include: 3α-hydroxy-3β-(4-hydroxybutynyl)-21-(pyrid-4-ylthio)-5β-pregnan-20-one; 3α-hydroxy-21-(pyrid-4-yloxy)-5β-pregnan-20-one; 3α-hydroxy-2β-propoxy-21-thiopropanesulfonate-5α-pregnan-20-one sodium salt; 3β-ethynyl-3α-hydroxy-21-(3'-hydroxypropylthio))-5β-pregnan-20-one; 3β-ethynyl-3α-hydroxy-21-(thiopropanesulfate)-5β-pregnan-20-one sodium salt; 3α-hydroxy-2β-propoxy-21-(pyrid-4-ylthio)-5α-pregnan-20-one N-methyl iodide; 3α-hydroxy-21-(2'-hydroxyethylthio)-5β-pregnan-20-one; 3β-ethynyl-3α-hydroxy-21-(2'-hydroxyethylthio)-5β-pregnan-20-one; 3α-hydroxy-21-(pyrid-4-ylthio)-5α-pregnan-20-one N-methyl iodide; 3α-hydroxy-21-(pyrid-4-ylthio)-5β-pregnan-20-one N-methyl iodide; 3β-ethynyl-3α-hydroxy-21-thioethanesulfate-5β-pregnan-20-one trimethylammonium salt; 3α-hydroxy-3β-methoxymethyl-21-(pyrid-4-ylthio)-5α-pregnan-20-one; 21-(4'-aminophenylthio)-3α-hydroxy-3β-methoxymethyl-5α-pregnan-20-one; 21-(4'-dimethylaminophenylthio)-3α-hydroxy-3β-methoxymethyl-5α-pregnan-20-one; 3α-hydroxy-3β-methoxymethyl-21-(4'-nitrophenylthio)-5α-pregnan-20-one; 3α-hydroxy-3β-methoxymethyl-21-(4'-nitrophenylsulfinyl)-5α-pregnan-20-one; 3α-hydroxy-3β-methoxymethyl-21-(4'-nitrophenylsulfonyl)-5α-pregnan-20-one; 21-(4'-dimethylaminophenoxy)-3α-hydroxy-3β-methyl-5α-pregnan-20-one; 3α-hydroxy-3β-methyl-21-(4'-nitrophenoxy)-5α-pregnan-20-one; 3α-hydroxy-3β-methyl-21-(4'-trimethylammoniumphenoxy)-5α-pregnan-20-one iodide salt; 3β-ethynyl-3α-hydroxy-21-thiopropanesulfonate-5β-pregnan-20-one sodium salt; 3β-ethynyl-3α-hydroxy-21-(3'-hydroxypropylsulfonyl))-5β-pregnan-20-one; 3α-hydroxy-21-(3'-hydroxypropylthio))-2β-propoxy-5α-pregnan-20-one; 3α-hydroxy-21-(3'-hydroxypropylsulfonyl))-2β-propoxy-5α-pregnan-20-one; 3α-hydroxy-2β-propoxy-21-sulfonylpropanesulfate-5α-pregnan-20-one sodium salt; 21-(4'-fluorophenylthio)-3α-hydroxy-3β-methoxymethyl-5α-pregnan-20-one; 3β-ethynyl-3α-hydroxy-21-(pyrid-4-ylthio)-5α-pregnan-20-one; 3β-(4'-acetylphenyl)ethynyl-3α-hydroxy-21-(pyrid-4-ylthio)-5β-pregnan-20-one; 3α-hydroxy-2β-propoxy-21-(4'-N,N,N-trimethylaimmoniumphenoxy)-5α-pregnan-20-one iodide salt; 3α-hydroxy-3β-methyl-21-(quinolin-6-yloxy)-5α-pregnan-20-one N-methyl iodide; 3α-hydroxy-3β-methyl-21-(quinolin-6-yloxy)-5α-pregnan-20-one; 21-(4'-fluorophenyl)sulfonyl-3α-hydroxy-3β-methoxymethyl-5α-pregnan-20-one; and 3α-hydroxy-3β-methoxymethyl-21-(4'-pyrrolidinophenyl)sulfonyl-5α-pregnan-20-one.

The more preferred neuroactive steroids according to this aspect of the present invention include 3α-hydroxy-3β-(4'-hydroxybutynyl)-21-(pyrid-4-ylthio)-5β-pregnan-20-one; 3α-hydroxy-21-(pyrid-4-yloxy)-5β-pregnan-20-one; 3α-hydroxy-2β-propoxy-21-thiopropanesulfonate-5α-pregnan-20-one sodium salt; 3β-ethynyl-3α-hydroxy-21-(3'-hydroxypropylthio))-5β-pregnan-20-one; 3α-hydroxy-3β-methoxymethyl-21-(pyrid-4-ylthio)-5α-pregnan-20-one; 3α-hydroxy-3β-methoxymethyl-21-(4'-nitrophenylsulfinyl)-5α-pregnan-20-one; 3β-hydroxy-3β-methoxymethyl-21-(4'-nitrophenylsulfonyl)-5α-pregnan-20-one; 3α-hydroxy-3β-methyl-21-(4'-nitrophenoxy)-5α-pregnan-20-one; 3α-hydroxy-21-(3'-hydroxypropylthio))-2β-propoxy-5α-pregnan-20-one; 3α-hydroxy-21-(3'-hydroxypropylsulfonyl))-2β-propoxy-5α-pregnan-20-one; and 3α-hydroxy-2β-propoxy-21-sulfonylpropanesulfate-5α-pregnan-20-one sodium salt.

The especially preferred neuroactive steroids according to this aspect of the present invention include 3α-hydroxy-3β-(4-hydroxybutynyl)-21-(pyrid-4-ylthio)-5β-pregnan-20-one; 3α-hydroxy-3β-methoxymethyl-21-(pyrid-4-ylthio)-5α-pregnan-20-one; 3α-hydroxy-21-(3'-hydroxypropylsulfonyl))-2β-propoxy-5α-pregnan-20-one; and 3α-hydroxy-21-(pyrid-4-yloxy)-5β-pregnan-20-one.

Diastereomers

It will be obvious to one skilled in the art that the above described compounds may be present as mixtures of diastereomers which may be separated into individual diastereomers. Resolution of the diastereomers may be conveniently accomplished by gas or liquid chromatography or isolation from natural sources. Unless otherwise specified herein, reference in the specification and claims to the compounds of the invention, as discussed above, is intended to include all isomers, whether separated or mixture thereof.

Where isomers are separated, the desired pharmacological activity will often predominate in one of the diastereomers. As disclosed herein, these compounds display a high degree of stereospecificity. In particular, those compounds having the greatest affinity for the GABA receptor complex are those with 3β-substituted-3α-hydroxypregnane steroid skeletons.

Synthetic Methods

The compounds according to the invention may be prepared by any convenient method, e.g., using conventional techniques such as are described in Djerassi, *Steroid Reactions*, Holden-Day, Inc., San Francisco (1963), or Fried and Edwards, *Organic Reactions in Steroid Chemistry*, Van Nostrand-Reinhold Co., New York (1972).

The C17 ethers of the present invention are prepared from 17β-hydroxy compounds by methods well known to those skilled in the art for preparing ethers from the corresponding alcohols. Most of these methods are described in Larock, *Comprehensive Organic Transformations* VCH Publishers, New York (1989). The 17β-hydroxy starting materials are well known to those skilled in the art. It is advisable to protect the 3-keto group by prior formation of a ketal. The ketal may then be reacted by known methods to form the C17 ether and the ketal hydrolyzed to obtain the 3-keto-17-ether compounds. Various nucleophiles can be added to the 3-one of these compounds to obtain the 3β-substituted-3α-hydroxy-C17-ether derivatives.

Another method to obtain the C17 ethers is by the reaction of C17-ketals, obtained from the corresponding C17-ones, with lithium aluminum hydride and $AlCl_3$ as described by Cross et al., *Steroids* 5:557 (1965).

The phenylethynyl substituents can be prepared by palladium (Pd) catalyzed coupling of the corresponding ethynyl derivatives with phenyliodides or phenylbromides in the presence of an amine.

The C21 bromides, used as starting materials in the examples, were all prepared using the procedure for preparing alpha-bromo-ketones from methyl ketones. This procedure is well known to those of ordinary skill in the art.

Pharmaceutical Uses

The compounds of and used in the invention, that being the nontoxic, pharmaceutically acceptable, natural and synthetic, direct acting and "prodrug" forms of steroid derivatives, have hitherto unknown activity in the brain at the $GABA_A$ receptor complex. The present invention takes advantage of the discovery of this previously unknown mechanism and activity.

The pharmaceutical compositions of this invention are prepared in conventional dosage unit forms by incorporating an active compound of the invention or a mixture of such compounds, with a nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount, selected from about 1 mg to about 500 mg of active ingredient per dosage unit. This quantity depends on the specific biological activity desired and the condition of the patient.

The pharmaceutical carrier employed may be, for example, either a solid, liquid, or time release (see e.g. *Remington's Pharmaceutical Sciences*, 14th Edition (1970)). Representative solid carriers are lactose, terra alba, sucrose, talc, gelatin, agar, pectin, acacia, magnesium stearate, stearic acid, microcrystalline cellulose, polymer hydrogels and the like. Typical liquid carriers are propylene glycol, glycofurol, aqueous solutions of cyclodextrins, syrup, peanut oil, and olive oil and the like emulsions. Similarly, the carrier or diluent may include any time-delay material well known to the art, such as glycerol monostearate or glycerol distearate alone or with wax, microcapsules, microspheres, liposomes, and/or hydrogels.

A wide variety of pharmaceutical forms can be employed. Thus, when using a solid carrier, the preparation can be plain milled micronized, in oil, tableted, placed in a hard gelatin or enteric-coated capsule in micronized powder or pellet form, or in the form of a troche or lozenge. The compounds of the present invention may also be administer in the form of suppositories for rectal administration. Compounds may be mixed in material such as cocoa butter and polyethylene glycols or other suitable non-irritating material which is solid at room temperature but liquid at the rectal temperature. When using a liquid carrier, the preparation can be in the form of a liquid, such as an ampule, or as an aqueous or nonaqueous liquid suspension. Liquid dosage forms also need pharmaceutically acceptable preservatives. In addition, because of the low doses required, as based on the data disclosed herein, parental administration, nasal spray, sublingual and buccal administration, and timed release skin patches are also suitable pharmaceutical forms for topical administration.

The method of producing anxiolytic, anticonvulsant, mood altering (such as anti-depressant) or hypnotic activity, in accordance with this invention, comprises administering to a subject in need of such activity a compound of the invention, usually prepared in a composition as described above with a pharmaceutical carrier, in a nontoxic amount sufficient to produce said activity.

During menses, the levels of excreted progesterone metabolites vary approximately fourfold (Rosciszewska et al., *J. Neurol. Neurosurg. Psych.* 49:47–51 (1986)). Therefore, therapy for controlling symptoms involves maintaining the patient at a higher level of progesterone metabolites than normal in the premenstrual state of PMS patients. Plasma levels of active and major metabolites are monitored during pre-menses and post-menses of the patient. The amount of the compounds of the invention administered, either singly or as mixtures thereof are thus calculated to reach a level which will exert $GABA_A$-receptor activity equal or higher than the level of progesterone metabolites in the normal subject during the premenses state.

The method of inducing sleep and maintaining substantially the level of REM sleep that is found in normal sleep, wherein substantial rebound insomnia is not induced, in accordance with the present invention, comprises administering to a subject in need of such activity an effective amount of a steroid derivative described herein. The compounds of the invention are able to increase NREM sleep and the total sleep period, without substantially affecting the amount of REM sleep. Rebound insomnia is defined as the reduction of NREM sleep after the hypnotic action of the treatment has returned to control levels. Methods for evaluating the effects of the compounds of the invention on REM and NREM sleep are disclosed in WO94/27608, published Dec. 8, 1994, the contents of which are fully incorporated by reference herein.

The mute of administration may be any route that effectively transports the active compound to the $GABA_A$ receptors that are to be stimulated. Administration may be carried out parenterally, enterally, rectally, intravaginally, intradermally, intramuscularly, sublingually, or nasally; the oral intramuscular, and dermal routes are preferred. For example, one dose in a skin patch may supply the active ingredient to the patient for a period of up to one week. However, the parenteral route is preferred for status epilepticus.

The following examples are illustrative, but not limiting, of the method and compositions of the present invention. Other suitable modifications and adaptations of the variety of conditions and parameters normally encountered and obvious to those skilled in the art are within the spirit and scope of the invention.

19

EXAMPLE 1

3α-Hydroxy-17β-methoxy-3β-(3'-methylbut-3'-en-1'-ynyl)-5β-androstane

A solution of 2-methyl-1-buten-3-yne (150 mg, 0.21 mL, 2.25 mmol) in dry THF (20 mL) was treated with n-BuLi (2.5M in THF, 2.25 mmol, 0.9 mL) at −70° C. After stirring the mixture at −75° C. for 0.5 hr, a solution 17β-methoxy-5β-androstan-3-one (228 mg, 0.75 mmol) in THF (20 mL) was added and the mixture was stirred at −78° C. for 30 min. The cooling bath was removed and the mixture was quenched with NH$_4$Cl solution (2 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (9:1) gave 3α-hydroxy-17β-methoxy-3β-(3'-methylbut-3'en-1'-ynyl)-5β-androstane (133 mg) as a colorless solid; mp 145–147° C.; TLC R$_f$ (hexane:acetone 85:15)=0.21.

EXAMPLE 2

3α-(4'-Hydroxy-1'-butynyl)-3β-hydroxy-17β-methoxy-5β-androstane and 3β-(4'-Hydroxy-1'-butynyl)-3α-hydroxy-17β-methoxy-5β-androstane A solution of 3-butyn-1-ol (0.114 mL, 1.5 mmol) in dry THF (15 mL) was treat with n-BuLi (1.2 mL, 2.5M in THF, 3 mmol) at −75° C. After stirring the mixture at −78° C. for 0.5 hr, a solution of 17β-methoxy-5β-androstan-3-one (152 mg, 0.5 mmol) in THF (20 mL) was added and the mixture was stirred at −78° C. for 5 min. The cooling bath was then removed and the stirring was continued at room temperature for 45 min. The mixture was then quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (4:1) gave 3α-(4'-hydroxy-1'-butynyl)-3β-hydroxy-17β-methoxy-5β-androstane (20 mg), and then 3β-(4'-hydroxy-1'-butynyl)-3α-hydroxy-17βmethoxy-5β-androstane (70 mg) as a colorless solid; mp 132–134° C.; TLC R$_f$ (toluene:acetone 4:1)=0.19.

EXAMPLE 3

3β-(4'-Hydroxy-1'-butynyl)-3α-hydroxy-17β-methoxy-5α-androstane 4'-hemisuccinate and sodium salt thereof A solution of 3β-(4'-hydroxy-1'-butynyl)-3α-hydroxy-17β-methoxy-5α-androstane (350 mg, 0.93 mmol) in pyridine (6 mL) was treated with succinic anhydride (372 mg, 3.7 mmol) and 4-(N,N-dimethyl)aminopyridine (20 mg). The mixture was heated to 70–75° C. for 3 hr. The TLC showed 100% conversion. It was cooled to room temperature and was poured into ice-2N HCl. The organics were extracted with EtOAc. The organic layer was washed with 0.2N HCl, water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (7:3) gave 3β-(4'-hydroxy-1'-butynyl)-3α-hydroxy-17β-methoxy-5α-androstane 4'-hemisuccinate (360 mg).

A mixture of the above hemisuccinate (360 mg 0.76 mmol), NaHCO$_3$ (64 mg 0.76 mmol), water (3 mL), and CH$_2$Cl$_2$ (5 mL) was stirred at room temperature for 1 hr. The solvent was removed and the residue was suspended in acetone (5 mL). The white solid was then collected by filtration and dried to yield the sodium salt as a colorless solid (210 mg).

EXAMPLE 4

3β-(4'-Hydroxy-1-'-butynyl)-3α-hydroxy-17β-methoxy-5α-androstane and 3α-(4'-Hydroxy-1'-butynyl)-3β-hydroxy-17β-methoxy-5α-androstane A solution of 3-butyn-1-ol (0.15 mL, 2 mmol) in dry THF (15 mL) was treated with n-BuLi (1.6 mL, 2.5M in THF, 4 mmol) at −75° C. After stirring the mixture at −78° C. for 0.5 hr, a solution of 17β-methoxy-5α-androstan-3-one (304 mg, 1 mmol) in THF (20 mL) was added and the mixture was stirred at −78° C. for 5 min. The cooling bath was then removed and the stirring was continued at room temperature for 45 min. The mixture was then quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (4:1) gave 3β-(4'-hydroxy-1'-butynyl)-3α-hydroxy-17β-methoxy-5α-androstane (50 mg); mp 184–186° C.; TLC R$_f$ (toluene:acetone 4:1)=0.35; and then 3α-(4'-hydroxy-1'-butynyl)-3β-hydroxy-17β-methoxy-5α-androstane (225 mg) as a colorless solid; mp 185–187° C.; TLC R$_f$ (toluene acetone 4:1)=0.24.

EXAMPLE 5

3α-Hydroxy-17β-methoxy-3βmethyl-5α-androstane and 3β-Hydroxy-17β-methoxy-3α-methyl-5α-androstane A solution of 17β-methoxy-5α-androstan-3-one (101 mg, 0.33 mmol) in dry THF (20 mL) was treated with MeLi (1 mL, 1.5M in THF, 1.5 mmol) at −75° C. After stirring the mixture at −78° C. for 0.5 hr, the mixture was quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (95:5) gave 3β-methyl-3α-hydroxy-17β-methoxy-5α-androstane (35 mg); mp 151–154° C.; TLC F$_f$ (hexane:acetone 7:3)=0.43; and then 3α-methyl-3β-hydroxy-17β-methoxy-5α-androstane (30 mg) as a colorless solid; TLC R$_f$ (hexane:acetone 7:3)=0.27.

EXAMPLE 6

3α-Hydroxy-17β-methoxy-3β-trifluoromethyl-5α-androstane and 3β-Hydroxy-17βmethoxy-3α-trifluoromethyl-5α-androstane A solution of 17β-methoxy-5α-androstan-3-one (220 mg, 0.75 mmol) in dry THF (20 mL) was treated wit trifluoromethyltrimethylsilane (3 mL, 0.5M in THF, 1.5 mmol), and tetrabutylammonium fluoride (TBAF) (10 mg) at 0° C. After stirring the mixture at 23° C. for 2 hr, the mixture was recooled to 0° C. A solution of TBAF (1M in THF, 2 mL, 2 mmol) was added. The mixture was stirred at room temperature for 10 min. quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:ethyl acetate mixture (9:1) gave 3β-trifluoromethyl-3α-hydroxy-17β-methoxy-5α-androstane (9 mg), TLC R$_f$ (hexane:EtOAc 8:2)=0.51; and then 3α-trifluoromethyl-3β-hydroxy-17β-methoxy-5α-androstane (170 mg) as a colorless solid; TLC R$_f$ (hexane:EtOAc 8:2)=0.45.

EXAMPLE 7

3β-Hydroxy-17β-methoxy-3β-trifluoromethyl-5β-androstane

A solution of 17β-methoxy-5β-androstan-3-one (304 mg, 1 mmol) in dry THF (20 mL) was treated with trifluoromethyltrimethylsilane (7 mL, 0.5M in THF, 3.5 mmol), and TBAF (10 mg) at 0° C. After stirring the mixture at 23° C. for 2 hr, the mixture was recooled to 0° C. A solution of TBAF (1M in THF, 3.5 mL, 3.5 mmol) was added. The mixture was stirred at room temperature for 10 min. and then quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:ethyl acetate mixture (9:1) gave 3β-trifluoromethyl-3α-hydroxy-17β-methoxy-5β-androstane (220 mg); mp 122–127° C.; TLC R$_f$ (hexane:EtOAc 8:2)=0.38.

EXAMPLE 8

3α-Hydroxy-17β-methoxy-5β-androstane

A solution of 17β-methoxy-5β-androstan-3-one (130 mg, 0.42 mmol) in dry THF (15 mL) was treated with lithium tri(tert-butoxy)aluminum hydride (1 mL, 1M in THF, 1 mmol) at −73° C. After stirring the mixture at −75° C. for 3 hr and then at −10° C. for 1.5 hr, the mixture was quenched with NaOH solution (1N, 2 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (9:1) gave 3α-hydroxy-17β-methoxy-5β-androstane (107 mg); mp 151–156° C.; TLC R$_f$ (hexane:acetone 7:3)=0.18.

EXAMPLE 9

17β-(2-Propynyloxy)-5α-androstan-3-one

A solution of 17β-hydroxy-5α-androstan-3-one cyclic 3-(1,2-ethanediyl acetal) (1.03 g, 3 mmol) in dry THF (20 mL) was treated with KOt-Bu (12 mL, 1M in THF, 12 mmol) at 23° C. After stirring the mixture at 55° C. for 2.5 hr, it was cooled to −50° C. Propargyl bromide (80% solution in toluene, 1.3 mL, 11 mmol) was added and the stirring was continued at 50–55° C. for 2.5 hr. The solvents were removed and the residue was treated with acetone (25 mL). After acidifying with 2N HCl, it was stirred at room temperature for 15 hr. The mixture was neutralized with 2N NaOH solution. The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (8:2) gave 17β-(2-propynyloxy)-5α-androstan-3-one (700 mg).

EXAMPLE 10

3α-Hydroxy-3β-methyl-17β-(2-propynyloxy)-5α-androstane and 3β-Hydroxy-3α-methyl-17β-(2-propynyloxy)-5α-androstane A solution of 17β-propynyloxy)-5α-androstan-3-one (230 mg, 0.7 mmol) in dry THF (20 mL) was treated with MeLi (5 mL, 1M in THF, 5 mmol) at −70° C. After stirring the mixture at −70° C. for 0.5 hr, the cooling bath was removed and it was warmed to 10° C. The mixture was then quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (98:2) gave 3α-hydroxy-3β-methyl-17β-(2-propynyloxy)-5α-androstane (40 mg); TLC R$_f$ (toluene:acetone 95:5)=0.31; and then 3β-hydroxy-3α-methyl-17β-(2-propynyloxy)-5α-androstane (70 mg) as a colorless solid; TLC R$_f$ (hexane:acetone 7:3)=0.27.

EXAMPLE 11

17β-[3-(4-Acetylphenyl)-2-propynyloxy]-3α-hydroxy-3β-methyl-5α-androstane

A solution of 4-iodoacetophenone (16 mg, 0.06 mmol), 3α-hydroxy-3β-methyl-17β-(2-propynyloxy)-5α-androstane (22 mg, 0.06 mmol) in dry degassed triethylamine (1 mL) was stirred under argon at 23° C. Bis (triphenylphosphine)palladium chloride (2 mg) and CuI (2 mg) were added and the mixture was stirred at this temp. for 45 min. CH$_2$Cl$_2$ (4 mL) was added and the mixture was stirred at 23° C. for 1 hr. The TLC showed 100% conversion of the starting material, hence, the solvent was removed and the residue was purified by chromatography on silica gel. Elution with hexane:acetone (85:15) gave 17β-[3-(4-acetylphenyl)-2-propynyloxy]-3α-hydroxy-3β-methyl-5α-androstane (19 mg) as a colorless solid; mp 52–55° C.; TLC R$_f$ (hexane:acetone 85:15)=0.15.

EXAMPLE 12

17β-(2-Hydroxyethoxy)-3α-hydroxy-5α-androstane

A solution of 3α-hydroxy-5α-androstan-17-one cyclic 17-(1,2-ethanediyl acetal) (166 mg, 0.5 mmol) in dry THF (10 mL) was treated with LAH (18 mg, 0.5 mmol) and AlCl$_3$ (266 mg, 2 mmol) at 23° C. After stirring the mixture at 45° C. for 2 hr, it was quenched with NH$_4$Cl solution (2 mL). The solvents were removed and the residue was extracted with EtOAc. The organic layer was washed with dil. HCl, water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (8:2) gave 17β-(2-hydroxyethoxy)-3α-hydroxy-5α-androstane (123 mg); mp 181–183° C.; TLC R$_f$ (hexane:acetone 7:3)=0.31.

EXAMPLE 13

3βEthynyl-3α-hydroxy-17β-methoxy-5-β-androstane

A solution of 1,2-dibromoethylene (1.6 mL, 3.7 g, 19.71 mmol) in dry THF (10 mL) was treated with n-BuLi (16.4 mL, 2.4M in THF, 39.4 mmol) at −75° C. After stirring the mixture at −78° C. for 0.25 hr, a solution of 17β-methoxy-5β-androstan-3-one (2 g, 6.57 mmol) in THF (20 mL) was added and the mixture was stirred at −78° C. for 15 min. The cooling bath was then removed and the mixture was quenched with NH$_4$Cl solution (3 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (95:5) gave 3β-ethynyl-3α-hydroxy-17β-methoxy-5β-androstane (1.70 g) as a colorless solid; mp 62–65° C.; TLC R$_f$ (toluene:acetone 95:5)=0.23.

EXAMPLE 14

3β-(4'-Aceylphenylethynyl)-3α-hydroxy-17β-methoxy-5β-androstane

A solution of 4-iodoacetophenone (112 mg, 0.45 mmol) and 3β-ethynyl-3α-hydroxy-17β-methoxy-5β-androstane (150 mg, 0.45 mmol) in dry degassed triethylamine (1 mL) was stirred under argon at 23° C. Bis(triphenylphosphine) palladium chloride (5 mg) and CuI (5 mg) were added and the mixture was stirred at this temp. for 45 min. CH$_2$Cl$_2$ (5 mL) was added and the mixture was stirred at 23° C. for 1 hr. The TLC showed 100% conversion of the starting material, hence, the solvent was removed and the residue was purified by chromatography on silica gel. Elution with hexane:EtOAc (7:3) gave 3β-(4'-acetylphenylethynyl)-3α-hydroxy-17β-methoxy-5β-androstane (130 mg) as a colorless solid; mp 189–191° C.; TLC R$_f$ (hexane:acetone 4:1)=0.31.

EXAMPLE 15

3α-Ethynyl-3β-hydroxy-17β-methoxy-5α-androstane and 3β-Ethynyl-3α-hydroxy-17β-methoxy-5α-androstane A solution of 1,2-dibromoethylene (1.7 mL, 21 mmol) in dry THF (25 mL) was treated with n-BuLi (16.8 mL, 2.5 M in THF, 42 mmol) at −65° C. After stirring the mixture at −70° C. for 0.25 hr, a solution of 17β-methoxy-5α-androstan-3-one (2.128 g, 7 mmol) in THF (22 mL) was added and the mixture was stirred at −78° C. for 30 min. The cooling bath was then removed and the mixture was quenched with NH$_4$Cl solution (3 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (95:5) gave 3β-ethynyl-3α-hydroxy-17β-methoxy-5β-androstane (100 mg) as a colorless solid; mp 138–145° C.; TLC R$_f$ (hexane:acetone 7:3)=0.45; and then 3α-ethynyl-3β-hydroxy-17β-methoxy-5β-androstane (1.6 g) as a colorless solid.

EXAMPLE 16

3β-Ethynyl-3α-hydroxy-17β-methoxy-19-nor-5β-androstane

A solution of 1,2-dibromoethylene (0.9 mL, 2.0 g, 10.85 mmol) in dry THF (10 mL) was treated with n-BuLi (9 mL, 2.4M in THF, 21.7 mmol) at −75° C. After stirring the mixture at −78° C. for 0.25 hr, a solution of 17β-methoxy-19-nor-5β-androstan-3-one (1 g, 3.62 mmol) in THF (20 mL) was added and the mixture was stilted at −78° C. for 20 min. The cooling bath was then removed and the mixture was quenched with NH$_4$Cl solution (3 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (98:2) gave 3β-ethynyl-3α-hydroxy-17β-methoxy-19-nor-5β-androstane (750 mg) as a colorless solid; mp 152–154° C.; TLC R$_f$ (hexane:acetone 7:3)=0.58.

EXAMPLE 17

3β-(4'-Acetylphenylethynyl)-3α-hydroxy-17β-methoxy-19-nor-5β-androstane

A solution of 4-iodoacetophenone (117 mg, 0.47 mmol) and 3β-ethynyl-3α-hydroxy-17β-methoxy-19-nor-5β-androstane (150 mg, 0.47 mmol) in dry degassed triethylamine (1 mL) was stirred under argon at 23° C. Bis (triphenylphosphine)palladium chloride (5 mg) and CuI (5 mg) were added and the mixture was stirred at this temp. for 45 min. CH$_2$Cl$_2$ (5 mL) was added and the mixture was stirred at 23° C. for 1 hr. The TLC showed 100% conversion of the staring material, hence, the solvent was removed and the residue was purified by chromatography on silica gel. Elution with toluene:acetone (95:5) gave 3β-(4'-acetylphenylethynyl)-3α-hydroxy-17β-methoxy-19-nor-5β-androstane (105 mg) as a colorless solid; mp 148–150° C.; TLC R$_f$ (hexane:acetone 4:1)=0.52.

EXAMPLE 18

3α-Hydroxy-17β-methoxy-3β-trifluoromethyl-19-nor-5β-androstane

A solution of 17β-methoxy-19-nor-5β-androstan-3-one (300 mg, 1.08 mmol) in dry THF (15 mL) was treated with trifluoromethyltrimethylsilane (5 mL, 0.5M in THF, 2.5 mmol), and TBAF (5 mg) at 0° C. After stirring the mixture at 23° C. for 2 hr, the mixture was recooled to 0° C. A solution of TBAF (1M in THF, 3.5 mL, 3.5 mmol) was added. The mixture was stirred at room temperature for 10 min. and then quenched with NH$_4$Cl solution (5 mL). The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (9:1) gave 3α-hydroxy-17β-methoxy-3β-trifluoromethyl-19-nor-5β-androstane (210 mg); mp 40–42° C.; TLC $R_f$ (hexane:acetone 7:3)=0.66.

EXAMPLE 19

3(R)-Spiro-2'-oxirane-17β-methoxy-5α-androstane

A solution of trimethylsulfoxonium iodide (2.42 g, 11 mmol) and KOt-Bu (1.12 g, 10 mmol) in dry THF (40 mL) was refluxed for 2 hr. After cooling to room temperature, 17β-methoxy-5α-androstan-3-one (2.432 g, 8 mmol) was added and the mixture was stirred at this temperature for 3 hr. It was then quenched with water (5 mL). The solvents were removed and the residue was extracted with EtOAc. The organic layer was washed with dil. HCl, water, and brine. After drying over anhyd. MgSO₄ the solution was filtered and evaporated to yield the crude 3(R)-spiro-2'-oxirane-17β-methoxy-5α-androstane (2.5 g). This crude product was then used as such for the next step.

EXAMPLE 20

3α-Hydroxy-17β-methoxy-3β-(2-propynyl)-5α-androstane

A solution of crude 3(R)-spiro-2'-oxirane-17β-methoxy-5α-androstane (318 mg, 1 mmol) and lithium acetylide. EDA (95%, 485 mg, 5 mmol) in DMSO (10 mL) was stirred at room temperature for 15 hr. It was then quenched with water (30 mL) and extracted with EtOAc. The organic layer was washed with water and brine. After drying over anhyd. MgSO₄ the solution was filtered and evaporated to yield the product This crude product was then dissolved in a small amount of $CH_2Cl_2$ and poured on a column of silica gel. Elution with hexane:acetone mixture (8:2) gave 3α-hydroxy-17β-methoxy-3β-(2-propynyl)-5β-androstane (200 mg); mp 145–150° C.; TLC $R_f$ (hexane:acetone 7:3)=0.6.

EXAMPLE 21

3α-Hydroxy-17β-methoxy-3β-methoxymethyl-5α-androstane

A solution of crude 3(R)-spiro-2'-oxirane-17β-methoxy-5α-androstane (318 mg, 1 mmol) and sodium (29 mg, 1.3 mmol) in MeOH (10 mL) was refluxed for 2.5 hr. It was then quenched with water (1 mL). The solvents were removed and the residue was extracted with EtOAc. The organic layer was washed with water, and brine. After drying over anhyd. MgSO₄ the solution was filtered and evaporated to yield the crude product This crude product was then dissolved in a small amount of $CH_2Cl_2$ and poured on a column of silica gel. Elution with hexane:acetone mixture (8:2) gave 3α-hydroxy-17β-methoxy-3β-methoxymethyl-5β-androstane (230 mg); mp 93–99° C.; TLC $R_f$ (hexane:acetone 7:3)=0.56.

EXAMPLE 22

3β-Chloromethyl-3α-hydroxy-17β-methoxy-5α-androstane

A solution of crude 3(R)-spiro-2'-oxirane-17β-methoxy-5α-androstane (318 mg, 1 mmol), tetramethylammonium chloride (166 mg, 1.5 mmol) and acetic acid (0.5 mL) in DMF (10 mL) was stirred at 90–95° C. for 2.5 hr. It was cooled to room temperature and then quenched with water (25 mL). After neutralizing with 2N NaOH, the mixture was extracted with EtOAc. The organic layer was washed with water, and brine. After drying over anhyd. MgSO₄ the solution was filtered and evaporated to yield the crude product. This crude product was then dissolved in a small amount of $CH_2Cl_2$ and poured on a column of silica gel. Elution with hexane:acetone mixture (95:5) gave 3β-chloromethyl-3α-hydroxy-17β-methoxy-5β-androstane (138 mg); mp 138–145° C.; TLC $R_f$ (hexane:acetone 8:2)=0.26.

EXAMPLE 23

3β-Ethenyl-3α-hydroxy-17β-methoxy-5α-androstane

A solution of trimethylsulfonium iodide (632 mg, 3.1 mmol) in dry THF (10 mL) was treated with n-BuLi (2.5M in THF, 3 mmol, 1.2 mL) at −5° C. After stirring the mixture at 0° C. for 0.5 hr, a solution 3(R)-spiro-2'-oxirane-17β-methoxy-5α-androstane (318 mg, 1 mmol) in THF (10 mL) was added. The cooling bath was removed and the mixture was stirred at room temperature for 2 h. It was then quenched with NH₄Cl solution (2 mL). The solvents were removed and the residue was extracted with EtOAc. The organic layer was washed with water, and brine. After drying over anhyd. MgSO₄ the solution was filtered and evaporated to yield the crude product. This crude product was then dissolved in a small amount of $CH_2Cl_2$ and poured on a column of silica gel. Elution with hexane:acetone mixture (7:3) gave 3β-ethenyl-3α-hydroxy-17β-methoxy-5β-androstane (220 mg) as a colorless solid; mp 104–111° C.; TLC $R_f$ (hexane:acetone 7:3)=0.5.

EXAMPLE 24

3α-Hydroxy-2β-isopropoxy-17β-methoxy-5α-androstane

A solution of 3α-hydroxy-2β-isopropoxy-5α-androstan-17-one 17-dimethyl acetal (prepared by the epoxide opening of 2α,3α-epoxy-5α-androstan-17-one with isopropoxide, followed by ketalization of 17-one) (490 mg, 1.25 mmol) in dry THF (15 mL) was treated with LAH (48 mg, 1.33 mmol) and AlCl₃ (332 mg, 2.5 mmol) at −30° C. After stirring the mixture at 23° C. for 1 hr, it was quenched with NH₄Cl solution (2 mL). The solvents were removed and the residue was extracted with EtOAc. The organic layer was washed with dil. HCl, water, and brine. After drying over anhyd. MgSO₄ the solution was filtered and evaporated to yield the crude product. This crude product was then dissolved in a small amount of $CH_2Cl_2$ and poured on a column of silica gel. Elution with hexane:acetone mixture (9:1) gave 3α-hydroxy-2β-isopropoxy-17β-methoxy-5α-androstane (43 mg) as a foam; TLC $R_f$ (hexane:acetone 7:3)=0.41.

EXAMPLE 25

3α-Hydroxy-3β-(4-hydroxybutynyl)-21-(pyrid-4-ylthio)-5β-pregnan-20-one

A solution of 21-bromo-3α-hydroxy-3β-(4-hydroxybutynyl)-5β-pregnan-20-one (230 mg, 0.494 mmol), 4-mercaptopyridine 90% (77 mg, 0.618 mmol), and triethylamine (86 μL, 0.618 mmol) in 10 mL of acetonitrile was stirred at room temperature for 3 h. The mixture was partitioned between EtOAc and water. The organic layer was washed with sat. aq. NaCl, dried with Na₂SO₄ and concentrated in vacuo. The crude residue was subjected to flash column chromatography. Elution with 35%→50% acetone in $CH_2Cl_2$ yielded 3α-hydroxy-3β-(4-hydroxybutynyl)-21-(pyrid-4-ylthio)-5β-pregnan-20-one (196 mg) as a yellow foam. TLC $R_f$ (acetone:$CH_2Cl_2$ 45:55)=0.36.

Similarly prepared were:

3α-hydroxy-21-(pyrid)-4-ylthio)-5β-pregnan-20-one; mp 193–195° C.; TLC $R_f$ (hexane:EtOAc 1:1)=0.11;

3α-hydroxy-21-(pyrid-4-ylthio)-5α-pregnan-20-one; m.p. 154–156° C.; TLC $R_f$ ($CH_2Cl_2$:acetone 4:1)=0.18;

3α-hydroxy-3β-methoxymethyl-21-(pyrid-4-ylthio)-5α-pregnan-20-one;

21-(4'-aminophenylthio)-3α-hydroxy-3β-methoxymethyl-5α-pregnan-20-one; mp 150–156° C.; TLC $R_f$ (hexane:EtOAc 3:1)=0.045;

3α-hydroxy-3β-methoxymethyl-21-(4'-nitrophenylthio)-5α-pregnan-20-one; TLC $R_f$ (hexane:EtOAc 3:1)=0.17;

21-(4'-fluorophenylthio)-3α-hydroxy-3β-methoxymethyl-5α-pregnan-20-one; TLC $R_f$ (hexane:acetone 85:15)=0.25;

3β-ethynyl-3α-hydroxy-21-(pyrid-4-ylthio)-5α-pregnan-20-one; TLC $R_f$ (hexane:EtOAc 1:1)=0.26; and 3β-(4'-acetylphenyl)ethynyl-3α-hydroxy-21-(pyrid-4ylthio)-5β-pregnan-20-one; TLC $R_f$ (hexane:EtOAc 2:1)=0.15.

EXAMPLE 26

3α-Hydroxy-21-(pyrid-4-yltio)-5β-pregnan-20-one N-methyl iodide

A solution of 3α-hydroxy-21-(pyrid-4-ylthio)-5β-pregnan-20-one (62 mg, 0.145 mmol) and 1 mL of methyl iodide in 5 mL of EtOAc was heated to reflux for a few hours until reaction complete by TLC. The mixture was then cooled to room temperature and concentrated in vacuo to a crude residue. The residue was triturated with ether and dried under vacuum to give 3α-hydroxy-21-(pyrid-4-ylthio)-5β-pregnan-20-one N-methyl iodide (70 mg) as an orange solid.

EXAMPLE 27

3α-Hydroxy-21-(pyrid-4-ylthio)-5α-pregnan-20-one N-methyl iodide

A solution of 3α-hydroxy-21-(pyrid-4-ylthio)-5α-pregnan-20-one (29 mg, 0.068 mmol) and 100 μL of methyl iodide in 5 mL of THF was heated to reflux. After 15 min. a solid precipitated and the refluxing was continued for a few hours. The mixture was cooled to room temperature and the excess methyl iodide allowed to evaporate. The solid was then filtered, washing with cold THF, resulting in 3α-hydroxy-21-(pyrid-4-ylthio)-5α-pregnan-20-one N-methyl iodide (26 mg) as a light orange solid.

EXAMPLE 28

3α-Hydroxy-2β-propoxy-21-(pyrid-4-ylthio)-5α-pregnan-20-one N-methyl iodide

A solution of 3α-hydroxy-2β-propoxy-21-(pyrid-4-ylthio)-5α-pregnan-20-one (50 mg, 0.103 mmol) and 130 μL of methyl iodide in 5 mL of THF was heated to reflux for a few hours until reaction complete by TLC. The mixture was then cooled to room temperature and concentrated in vacuo resulting in 3α-hydroxy-2β-propoxy-21-(pyrid-4-ylthio)-5α-pregnan-20-one N-methyl iodide (64 mg) as a light yellow solid.

Similarly prepared were:

3α-hydroxy-3β-methyl-21-(4'-trimethylammoniumphenoxy)-5α-pregnan-20-one iodide salt;

3α-hydroxy-2β-propoxy-21-(4'-N,N,N-trimethylammoniumphenoxy)-5α-pregnan-20-one iodide salt; and 3α-hydroxy-3β-methyl-21-(quinolin-6-yloxy)-5α-pregnan-20-one N-methyl iodide.

EXAMPLE 29

3β-Ethynyl-3α-hydroxy-21-hydroxyethylthio-5β-pregnan-20-one

A solution of 21-bromo-3β-ethynyl-3α-hydroxy-5β-pregnan-20-one (150 mg, 0.356 mmol), 2-mercaptoethanol (31 μL, 0.445 mmol), and triethylamine (62 μL, 0.445 mmol) in 5 mL of THF was stirred at room temperature overnight. The mixture was partitioned between EtOAc and water. The organic layer was washed with sat. aq. NaCl, dried with $Na_2SO_4$ and concentrated in vacuo resulting in 3β-ethynyl-3α-hydroxy-21-hydroxyethylthio-5β-pregnan-20-one (141 mg) as a white solid; mp 122–126° C.; TLC $R_f$ (hexane:acetone 3:1)=0.11.

Similarly prepared were:

3β-ethynyl-3α-hydroxy-21-hydroxypropylthio-5β-pregnan-20-one; TLC $R_f$ (hexane:acetone 3:1)=0.12;

3α-hydroxy-21-hydroxypropylthio-2β-propoxy-5α-pregnan-20-one; mp 133–136° C.; TLC $R_f$ (hexane:acetone 3:1)=0.175; and 3α-hydroxy-21-hydroxyethylthio-5β-pregnan-20-one; mp 150–152° C.

EXAMPLE 30

3β-Ethynyl-3α-hydroxy-21-thioethanoate-5β-pregnan-20-one sodium salt

A solution of 21-bromo-3β-ethynyl-3α-hydroxy-5β-pregnan-20-one (150 mg, 0.356 mmol), mercaptoacetic acid (31 μL, 0.445 mmol) and triethylamine (124 μL, 0.89 mmol) in 5 mL of DMF was stirred at room temperature for few hours. The mixture was partitioned between EtOAc and 2N HCl. The organic layer was washed with water, sat. aq. NaCl, dried with $Na_2SO_4$ and concentrated in vacuo to a residue. The residue was dissolved in 5 mL of $CH_2Cl_2$ and 1 eq. of sodium bicarbonate in 1 mL of water was added. The mixture was stirred for 30 min. and then concentrated to dryness under high vacuum resulting in 3β-ethynyl-3α-hydroxy-21-thioethanoate-5β-pregnan-20-one sodium salt (120 mg) as a white solid; Dec. >120° C.

Similarly prepared were:

3β-ethynyl-3α-hydroxy-21-thiopropanoate-5β-pregnan-20-one sodium salt;

3β-ethynyl-3α-hydroxy-21-thioethanesulfonate-5β-pregnan-20-one sodium salt; dec. >85° C.; TLC $R_f$ (chloroform:methanol 4:1)=0.25;

3β-ethynyl-3α-hydroxy-21-thiopropanesulfonate-5β-pregnan-20-one sodium salt; TLC $R_f$ (chloroform:methanol 4:1)=0.21; and 3α-hydroxy-2β-propoxy-21-thiopropanesulfonate-5α-pregnan-20-one sodium salt; TLC $R_f$ (chloroform:methanol 85:15)=0.22.

EXAMPLE 31

3β-Ethynyl-3α-hydroxy-21-thioethanesulfate-5β-pregnan-20-one trimthyl ammonium salt A solution of 3β-ethynyl-3α-hydroxy-21-hydroxyethylthio-5β-pregnan-20-one (140 mg, 0.335 mmol), sulfur trioxide trimethylamine complex (100 mg, 0.736 mmol), and sulfur trioxide pyridine complex (50 mg) in 4 mL of chloroform was stirred at room temperature overnight. The solid was filtered and the filtrate concentrated to a small volume. The residue was subjected to flash column chromatography. Elution with chloroform:methanol 85:15 resulted in 3β-ethynyl-3α-hydroxy-21-thioethanesulfate-5β-pregnan-20-one trimethyl ammonium salt (69 mg) as a solid; Dec. >120° C.

EXAMPLE 32

3β-Ethynyl-3α-hydroxy-21-thiopropanesulfate-5β-pregnan-20-one sodium salt

A solution of 3β-ethynyl-3α-hydroxy-21-hydroxypropylthio-5β-pregnan-20-one (50 mg, 0.115 mmol) and sulfur trioxide trimethylamine complex (19 mg, 0.139 mmol) in 0.5 mL of pyridine was stirred at room temperature overnight. The mixture was diluted with chloroform and washed with 2N HCl, sat. aq. NaCl, dried with $Na_2SO_4$ and concentrated in vacuo to a crude residue. The residue was subjected to flash column chromatography. Elution with chloroform:methanol 85:15 resulted in 3β-ethynyl-3α-hydroxy-21-thiopropanesulfate-5β-pregnan-20-one sodium salt (20 mg) as a solid; TLC $R_f$ (chloroform:methanol 85:15)=0.12.

Similarly prepared was 3α-hydroxy-2β-propoxy-21-sulfonylpropanesulfate-5α-pregnan-20-one sodium salt; TLC $R_f$ (chloroform:methanol 85:15)=0.15.

EXAMPLE 33

3β-Ethynyl-3α-hydroxy-21-hydroxpropylsulfinyl-5β-pregnan-20-one

A suspension of 3β-ethynyl-3α-hydroxy-21-hydroxypropylthio-5β-pregnan-20-one (90 mg, 0.208 mmol) and sodium periodate (~200 mg in 0.5 mL water) in methanol:THF 3:1 was stirred from 0° C. to room temperature overnight The mixture was concentrated to a small volume and partitioned EtOAc and water. The organic layer was washed with sat aq. NaCl, dried with $Na_2SO_4$ and concentrated in vacuo resulting in 3β-ethynyl-3α-hydroxy-21-hydroxypropylsulfonyl-5β-pregnan-20-one (83 mg) as a foam; TLC $R_f$ (hexane:acetone 2:1)=0.035.

Similarly prepared was 3α-hydroxy-2β-propoxy-21-sulfinylpropanesulfonate-5α-pregnan-20-one sodium salt.

EXAMPLE 34

3β-Ethynyl-3α-hydroxy-21-hydroxypropylsulfonyl-5β-pregnan-20-one

A solution of 3β-ethynyl-3α-hydroxy-21-hydroxypropylsulfinyl-5β-pregnan-20-one (65 mg, 0.145 mmol), mCPBA 57%–86% (42 mg), and a spatula of sodium bicarbonate in 5 mL $CH_2Cl_2$ was stirred from 0° C. to room temperature overnight. The mixture was partitioned between $CH_2Cl_2$ and aq. sodium bicarbonate. The organic layer was washed with sat. aq. NaCl, dried with $Na_2SO_4$, and concentrated in vacua to dryness resulting in 3β-ethynyl-3α-hydroxy-21-hydroxypropylsulfonyl-5β-pregnan-20-one (66 mg) as a white solid; TLC $R_f$ ($CH_2Cl_2$:acetone 1:1)=0.61.

Similarly prepared was 3α-hydroxy-21-(3'-hydroxypropylsulfonyl)-2β-propoxy-5α-pregnan-20-one; TLC $R_f$ (hexane:acetone 2:1)=0.26.

EXAMPLE 35

3β-Hydroxy-21-(pyrid-3-yl)oxy-5β-pregnan-20-one

To a solution of 3α-hydroxy-21-bromo-5β-pregnan-20-one (300 mg, 0.76 mmol) in DMF (5 mL) was added 3-hydroxypyridine (215 mg, 2.27 mmol) and $K_2CO_3$ (313 mg, 2.27 mmol) and the mixture obtained was sired at 25° C. for 0.5 h. The reaction mixture was then poured into a separatory funnel containing water (30 mL) and the mixture was extracted with EtOAc (3×35 mL). The combined extracts were washed with water (2×25 mL) and then dried over $Na_2SO_4$. Removal of the solvent in vacuo resulted in the crude product which was purified by flash chromatography over silica gel to yield the pure 3α-hydroxy-21-(pyrid-3-yl)oxy-5β-pregnan-20-one (50 mg); mp 63–66° C.; TLC $R_f$ (MeOH:$CH_2Cl_2$ 5:95)=0.15.

EXAMPLE 36

2β-Isopropoxy-3α-hydroxy-5α-androstane a. 2β-Isopropoxy-3α-hydroxy-5α-androstan-17-one tosylhydrazone To a mixture of 2β-isopropoxy-3α-hydroxy-5α-androstan-17-one (700 mg, 2.0 mmol) and p-toluenesulfonhydrazide (450 mg, 2.4 mmol) was added ethanol (2 mL) and the mixture obtained was heated to reflux for 12 h. Then the reaction mixture was dissolved in $CH_2Cl_2$ (150 mL) and washed with water (4×45 mL). It was then dried over $Na_2SO_4$ and removal of the solvent in vacuo resulted in the crude 2β-isopropoxy-3α-hydroxy-5α-androstan-17-one tosylhydrazone (1.113 g), which was used without further purification for the next step.

b. 2β-Isopropoxy-3α-hydroxy-5α-androstane

To a mixture of 2β-isopropoxy-3α-hydroxy-5α-androstan-17-one tosylhydazone (300 mg), $NaBH_3CN$ (144 mg) and p-toluenesulfonic acid (30 mg) was added DMF and sulfolane (1:1, 3 mL) and the mixture obtained was heated to 110° C. for 3 h. Then additional amount of $NaBH_3CN$ (144 mg) and p-toluenesulfonic acid (30 mg) was added and it was heated for another hour. Water was then added and the mixture was extracted with EtOAc (2×45 mL). The combined extracts were dried over $Na_2SO_4$ and the crude product obtained by removal of the solvent was purified by flash chromatography over silica gel to yield the pure 2β-isopropoxy-3α-hydroxy-5α-androstane (37 mg); TLC $R_f$ (EtOAc:hexane 1:9)=0.17.

EXAMPLE 37

3α-Hydroxy-5β-19-norandrostane a. 3α-Hydroxy-5β-19-norandrostan-17-one

To a solution of 5β-19-norandrostan-3,17-dione (0.76 g, 2.77 mmol) in THF (30 mL) at −78° C. was added a solution of lithium tri(tert-butoxy)aluminum hydride. The reaction mixture was then poured into a separatory funnel containing NHCl solution (50 mL) and the product was extracted with EtOAc (3×50 mL). The combined extracts were dried over $Na_2SO_4$ and removal of the solvent resulted in the crude product which was purified by flash chromatography over silica gel to yield the pure 3α-hydroxy-5β-19-norandrostan-17-one (605 mg); mp 159–161° C.; TLC $R_f$ (hexane:acetone 7:3)=0.30.

b. 3α-Hydroxy5β-19-norandrostane

To a mixture of 3α-hydroxy-5β-19-norandrostan-17-one (0.59 g, 2.13 mmol) and p-toluenesulfonylhydrazide (480 mg, 2.6 mmol) was added ethanol (2 mL) and the mi obtained was heated to reflux for 5 Then the reaction mixture was dissolved in $CH_2Cl_2$ (100 mL) and washed with water (2×30 mL). It was then dried over $Na_2O_4$ and removal of the solvent in vacuo resulted in the crude product (1.0 g). This crude product was mixed with $NaBH_3CN$ (555 mg) and p-toluenesulfonic acid (68 mg) and a mixture of DMF and sulfolane (1:11 10 mL) and the mixture obtained was heated to 130° C. for 2 h. Then additional amount of NaBH$_3$CN (200 mg) and p-toluenesulfonic acid (30 mg) was added and it was heated for another hour. Water (80 mL) was then added and the mixture was extracted with EtOAc (3×50 mL). The combined extracts were dried over Na$_2$SO$_4$ and the crude product obtained by removal of the solvent was purified by flash chromatography over silica gel to yield the pure 3α-hydroxy-5β-19-norandrostane (217 mg); mp 129–132° C.; TLC R$_f$ (EtOAc:hexane 1:9)=0.30.

EXAMPLE 38

3α-Hydroxy-3β-ethynyl-5β-19-norandrostane
a. 5β-19-Norandrostan-3-one

To a solution of 3α-hydroxy-5β-19-norandrostane (210 mg, 0.8 mmol) in CH$_2$Cl$_2$ (25 mL) was added NaOAc (100 mg, 1.2 mmol) and PCC (520 mg, 2.4 mmol) and the mixture obtained was stirred at 25° C. for 1 h. Then the reaction mixture was filtered through a pad of Florisil (15 g) in a Buchner funnel eluted with mixed solvent of ether and CH$_2$Cl$_2$ (1:1, 70 mL). The solvent was then removed in vacuo and the crude product thus obtained was purified by flash chromatography over silica gel to yield the pure 5β-19-norandrostan-3-one (190 mg); TLC R$_f$ (EtOAc:hexane 5:95)=0.20.

b. 3α-Hydroxy-3β-ethynyl-5β-19-norandrostane

To a solution of 1,2-dibromoethylene (410 mg, 2.2 mmol) was added n-BuLi (2.5 M, 1.8 mL, 4.4 mmol) at −78° C. and the reaction was stirred at this temperature for 45 min. Then a solution of 5β-19-norandrostan-3-one (190 mg, 0.73 mmol) in TBF (10 mL) was added dropwise to the generated lithium reagent. Then the reaction mixture was poured into a separatory funnel containing NH$_4$Cl solution (50 mL) and the product was extracted with EtOAc (3×40 mL). The combined extracts were dried over Na$_2$SO$_4$ and the crude product obtained by removal of the solvent was purified by flash chromatography over silica gel to yield the pure 3α-hydroxy-3β-ethynyl-5β-19-norandrostane (120 mg); m.p. 152–154° C.; TLC R$_f$ (EtOAc:hexane 1:9)=0.19.

EXAMPLE 39

3α-Hydroxy-3β-(4'-acetylphenyl)ethynyl-5β-19-norandrostane

To a mixture of 3α-hydroxy-3β-ethynyl-5β-19-norandrostane (120 mg, 0.42 mmol), 4-iodoacetophenone (115 mg, 0.46 mmol), bis(triphenylphosphine)palladium(II) chloride (catalytic amount) and copper(I) iodide (catalytic amount), was added triethylamine (1.5 mL) and the mixture obtained was stored under argon for 45 min with the flask wrapped with aluminum foil. Then CH$_2$Cl$_2$ (5 mL) was added and the reaction was stirred for 3 h. Then the solvent was removed in vacua and the residue was purified by flash chromatography over silica gel to yield the 3α-hydroxy-3β-(4'-acetylphenyl)ethynyl-5β-19-norandrostane (37 mg); TLC R$_f$ (EtOAc:hexane 15:85)=0.2.

EXAMPLE 40

3α-Isobutyryloxy-17β-methoxy-5β-androstane

A solution of 3α-hydroxy-17β-methoxy-5β-androstane (250 mg, 0.82 mmol) in dry pyridine (2 mL) was treated with isobutyryl chloride (0.12 mL, 1.15 mmol), and N,N-dimethylaminopyridine (5 mg) at 5° C. After stirring the mixture at 5–10° C. for 1 hr the mixture was quenched with HCl solution (0.5 N, 25 mL). The mixture was extracted with EtOAc. The organic layer was washed with dil. HCl, water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (9:1) gave 3α-isobutyryloxy-17β-methoxy-5β-androstane (266 mg); mp 82–87° C.; TLC R$_f$ (hexane:acetone 9:1)=0.6.

EXAMPLE 41

3α-Hydroxy-21-(pyrid-4-yloxy)-5β-pregnan-20-one

A solution of 21-bromo-3α-hydroxy-5β-pregnan-20-one (500 mg, 1.26 mmol), 4-hydroxypyridine (144 mg, 1.51 mmol), and triethyl amine (200 μL) in 10 mL of THF was heated under reflux for 4 h. The mixture was cooled to room temperature and partitioned between EtOAc and water. The organic layer was washed with sat. aq. NaCl, dried with MgSO$_4$ and concentrated in vacua. The crude residue was subjected to flash column chromatography. Elution with 50% acetone in CH$_2$Cl$_2$ yielded 3α-hydroxy-21-(pyrid-4-yloxy)-5β-pregnan-20-one (40 mg) as an oily solid; TLC R$_f$ (acetone:CH2Cl$_2$ 1:1)=0.28.

EXAMPLE 42

3α-Hydroxy-3β-methyl-21-(4'-nitrophenoxy)-5α-pregnan-20-one

A solution of 21-bromo-3α-hydroxy-3β-methyl-5α-pregnan-20-one (250 mg, 0.61 mmol), 4-nitrophenol (127 mg, 0.912 mmol), triethylamine (127 μL, 0.912 mmol), and a small amount of sodium iodide in 2:1 acetonitrile:DMF was stirred with heating to ~60° C. for 6 hours. The mixture was partitioned between EtOAc and 1:1 water:sat. aq. sodium bicarbonate. The organic layer was washed with 2N HCl, water and sat. aq. NaCl, dried with Na$_2$SO$_4$ and concentrated in vacuo. The crude residue was subjected to flash column chromatography. Elution with 20% acetone in hexane yielded 3α-hydroxy-3β-methyl-21-(4'-nitrophenoxy)-5α-pregnan-20-one (147 mg) as a solid; mp 169–172° C.; TLC R$_f$ (hexane:acetone 4:1)=0.35.

Similarly prepared was 3α-hydroxy-3β-methyl-21-(quinolin-6-yloxy)-5α-pregnan-20-one; TLC R$_f$ (hexane:acetone 3:1) =0.22.

EXAMPLE 43

21-(4'-Dimethylaminophenoxy)-3α-hydroxy-3β-methyl-5α-pregnan-20-one

A solution of 3α-hydroxy-3β-methyl-21-(4'-nitrophenoxy)-5α-pregnan-20-one (100 mg, 0.213 mmol), formaldehyde (37% solution in water, 800 mL), and 5% Pd/C (30 mg, catalytic) in ethanol was placed under H$_2$ atmosphere at 53 psi on a Parr shaker overnight The catalyst was filtered off washing with EtOAc, and the filtrate was washed in a separatory funnel with water and sat. aq. NaCl. The organic layer was then dried with Na$_2$SO$_4$ and concentrated in vacuo. The crude residue was subjected to flash column chromatography. Elution with 20% acetone in hexane yielded 21-(4'-dimethylaminophenoxy)-3α-hydroxy-3β-methyl-5α-pregnan-20-one (64 mg) as a foam; TLC R$_f$ (hexane:acetone 2:1)=0.55.

Similarly prepared was 21-(4'-dimethylaminophenylthio)-3α-hydroxy-3β-methoxymethyl-5α-pregnan-20-one; TLC R$_f$ (hexane:acetone 3:1)=0.35.

EXAMPLE 44

3α-Hydroxy-3β-methoxymethyl-21-(R)-(4'-nitrophenylsulfinyl)-5α-pregnan-20-one

3α-Hydroxy-3β-methoxymethyl-21-(S)-(4'-nitrophenylsidfinyl)-5α-pregnan-20-one; and 3α-Hydroxy-3β-methoxymethyl-21-(4'-nitrophenylsulfonyl)-5α-pregnan-20-one A solution of 3α-hydroxy-3β-methoxymethyl-21-(4'-nitrophenylthio)-5α-pregnan-20-one (120 mg, 0.23 mmol), mCPBA 57%–86% (111 mg), and NaHCO$_3$ (80 mg, 4 eq.) in CH$_2$Cl$_2$ was stirred from 0° C. to room temperature for 2 h. The reaction was partitioned between CH$_2$Cl$_2$ and aq. NaHCO$_3$. The organic layer was washed with sat. aq. NaCl then dried with Na$_2$SO$_4$ and concentrated in vacuo. The crude residue was subjected to flash column chromatography. Elution with 40%–5o% EtOAc in hexane yielded 3 0 α - h y d r o x y - 3 β - m e t h o x y m e t h y l - 2 1 - ( 4 ' - nitrophenylsulfonyl-5α-pregnan-20-one (65 mg) as a solid. TLC R$_f$ (hexane:EtOAc 1:1)=0.38, followed by 3 α - h y d r o x y - 3 β - m e t h o x y m e t h y l - 2 1 - ( R ) - ( 4 ' - nitrophenylsulfinyl)-5α-pregnan-20-one and 3α-hydroxy-3β-methoxymethyl-21-(S)-(4'-nitrophenylsulfinyl)-5α-pregnan-20-one in unidentifiable order.

Similarly prepared was 21-(4'-fluorophenyl)sulfonyl-3α-hydroxy-3β-methoxymethyl-5α-pregnan-20-one.

EXAMPLE 45

3α-Hydroxy-3β-methoxymnethyl-21-(4'-pyrrolidinophenyl)sulfonyl-5α-pregnan-20-one A solution of 21-(4'-fluorophenyl)sulfonyl-3α-hydroxy-3β-methoxymethyl-5α-pregnan-20-one (100 mg, 0.192 mmol) and pyrrolidine (21 μL, 0.25 mmol) in 5 mL of DMSO was heated on an oil bath at 100° C. for 5 hours, then stirred at rt overnight. Water was then added and the mixture was extracted with CH$_2$Cl$_2$. The organic phase was dried with Na$_2$SO$_4$ and concentrated in vacuo. The residue was subjected to flash column chromatography eluting with hexane:EtOAc to give the title compound (62 mg) as a yellow solid.

EXAMPLE 46

3α-Hydroxy-21-(4-pyridylmethylene)-5-β-pregnan-20-one

A solution of sodium ethoxide, prepared from 300 mg of sodium and 10 mL of ethanol, was added to a solution of 3α-hydroxy-5β-pregnan-20-one (500 mg, 1.57 mmol) and pyridine-4-carboxaldehyde (165 μL, 1.73 mmol) in 10 mL of ethanol via cannula. The mixture was stirred vigorously at rt for 30 hours. A solid precipitated out and was filtered and washed with ethanol, then dried under vacuum resulting in the title compound (260 mg).

EXAMPLE 47

3α-Hydroxy-21-(4-pyridylmethyl)-5β-pregnan-20-one

A solution of 3α-hydroxy-21-(4-pyridylmethylene)-5β-pregnan-20-one (100 mg, 0.245 mmol) in 4 mL each of ethanol and THF containing 20 mg of 5% Pd/C was subjected to hydrogen atmosphere via a balloon, and stirred for 5 hours. The catalyst was then filtered off and the solution concentrated in vacuo. The residue was subjected to flash column chromatography eluting with hexane:acetone to give the title compound (38 mg) as a solid; TLC R$_f$ (hexane:acetone 2:1)=0.28.

EXAMPLE 48

20,20-[2',3'-Bis(carboxy)ethylenedioxy]-3α-hydroxy-3β-trifuoromethyl-5β-19-norpregnane, dipotassium salt A mixture of 3α-hydroxy-3β-trifluoromethyl-5β-19-norpregnan-20-one (1.0 g, 2.68 mmol), dimethyl L-tartrate (1.0 g, 5.61 mmol), p-toluenesulfonic acid monohydrate (13 mg, 0.068 mmol) and trimethylorthoformate (0.35 ml) in 15 ml of toluene was heated at reflux with azeotropic removal of water. After 1 h, the reaction was allowed to cool to rt and solid NaHCO$_3$ (130 mg) was added. The resulting mixture was partitioned between a sat. aqueous NaHCO$_3$ solution and ethyl acetate. The aqueous layer was separated and washed twice with ethyl acetate (2×20 ml). The combined ethyl acetate layers were washed with a sat. NaCl solution, dried (Na$_2$SO$_4$) and concentrated in vacuo. The residue was chromatographed (17.5% acetone/hexane), giving a white foam which was triturated with hexane affording the dimethyl ester as a white solid. A solution of the diester in methanol (2 ml) and water (1 ml) was treated with solid KOH (78 mg): After stirring overnight, the reaction was concentrated to dryness giving the title compound as a light yellow solid.

EXAMPLE 49

Pharmacological Activity

Potency and Efficacy at the GRC Site

The in vitro and in vivo experimental data show that the naturally-occurring metabolites of progesterone/deoxycorticosterone and their derivatives interact with high affinity at a novel and specific recognition site on the GRC to facilitate the conductance of chloride ions across neuronal membranes sensitive to GABA (Gee, K. W. et al., *European Journal of Pharmacology*, 136:419–423 (1987); Harrison, N. L. et al., *J. Pharmacol. Exp. Ther*. 241:346–353 (1987)).

To those skilled in the art, it is known that the modulation of [$^{35}$S]t-butylbicyclophosphorothionate ([$^{35}$S]TBPS) binding is a measure of the potency and efficacy of drugs acting at the GRC, which drugs may be of potential therapeutic value in the treatment of stress, anxiety, and seizure disorders (Squires, R. F., et al., *Mol, Pharmacol*., 23:326 (1983); Lawrence, L. J., et al., *Biochem. Biophys. Res. Comm*., 123:1130–1137 (1984); Wood, et al., *Pharmacol, Exp. Ther*., 231:572–576 (1984)). Several experiments were performed previously to determine the nature of the modulation of [$^{35}$S]TBPS as affected by neuroactive steroids. It was found that these compounds interact with a novel site on the GRC which does not overlap with the barbiturate, the benzodiazepine or any other previously known sites. Furthermore, these compounds have high potency and efficacy at the GRC, with stringent structural requirements for such activity.

The procedures for performing this assay are fully discussed in: (1) Gee, K. W. et al., *European Journal of Pharmacology*, 136:419–423 (1987)); and (2) Gee, et al., *Molecular Pharmacology* 30:218 (1986). These procedures were performed as follows:

Brains from male Sprague-Dawley rats were removed immediately following sacrifice and the cerebral cortices dissected over ice. A P$_2$ homogenate was prepared as previously described (Gee, et al., *Molecular Pharmacology* 30:218 (1986)). Briefly, the cortices were gently homogenized in 032 M sucrose followed by centrifugation at 1000×g for 10 minutes. The supernatant was collected and centrifuged at 9000×g for 20 minutes. The resultant $P_2$ pellet was suspended as a 10% (original wet weight/volume) suspension in 50 mM Na/K phosphate buffer (pH 7.4) 200 mM NaCl to form the homogenate.

One hundred microliter (ml) aliquots of the $P_2$ homogenate (0.5 milligrams (mg) protein) were incubated with 2 nanomolar (nM) [$^{35}$S]TBPS (70–110 curies/millimole; New England Nuclear, Boston, Mass.) in the presence or absence of the naturally occurring steroids or their synthetic derivatives to be tested. The tested compounds were dissolved in dimethylsulfoxide (Baker Chem. Co., Phillipsburg, N.J.) and added to the incubation mixture in 5 μL aliquots. The incubation mixture was brought to a final volume of 1 mL with buffer. Non-specific binding was defined as binding in the presence of 2 mM TBPS. The effect and specificity of GABA (Sigma Chem. Co., St. Louis, Mo.) was evaluated by performing all assays in the presence of GABA plus (+)bicuculline (Sigma Chem. Co.). Incubations maintained at 25° C. for 90 minutes (steady state conditions) were terminated by rapid filtration through glass fiber filters (No. 32, Schleicher and Schuell, Keene, N.H.). Filter-bound radioactivity was quantitated by liquid scintillation spectrophotometry. Kinetic data and compound/[$^{35}$S]TBPS dose-response curves were analyzed by nonlinear regression using a computerized iterative procedure to obtain rate constants and $IC_{50}$ (concentration of compound at which half-maximal inhibition of basal [$^{35}$S]TBPS binding occurs) values.

Various compounds were screened to determine their potential as modulators of [$^{35}$S]TBPS binding in vitro. These assays were performed in accordance with the above discussed procedures. Based on these assays, we have established the structure-activity requirements for their specific interaction at the GRC and their rank order potency and efficacy. Experimental data obtained in this assay for a number of 3α-hydroxypregnan-20-one derivatives is discussed in Gee, K. W. et al., *European Journal of Pharmacology*, 136:419–423 (1987) and in U.S. Pat. No. 5,232,917. Table 1 provides $IC_{50}$ and maximum inhibition ($I_{MAX}$) measurements for numerous compounds, including examples of compounds disclosed and claimed herein. $IC_{50}$ is defined as concentration of compounds to inhibit 50% of control [$^{35}$S]TBPS binding. It is an indication of a compound's in vitro potency. Maximum inhibition is an indication of a compound's in vitro efficacy.

TABLE 1

| COMPOUND | $IC_{50}$ (nM) | IMAX (%) |
|---|---|---|
| 3β-(4'-Acetylphenyl)ethynyl-3α-hydroxy-17β-methoxy-19-nor-5β androstane | 8 | 96 |
| 3α-Hydroxy-2β-propoxy-21-(pyrid-4-ylthio)-5α-pregnan-20-one | 14 | 98 |
| 3α-Hydroxy-3β-(4-hydroxybutynyl)-21-(pyrid-4-ylthio)-5β-pregnan-20-one | 15 | 100 |
| 3β-(4'-Acetylphenyl)ethynyl-3α-hydroxy-17β-methoxy-5β-androstane | 20 | 104 |
| 3α-Hydroxy-21-(pyrid-4-ylthio)-5α-pregnan-20-one | 23 | 98 |
| 3β-(4'-Hydroxybutyn-1'-yl)-3α-hydroxy-17β-methoxy-5β-androstane | 26 | 105 |
| 3α-Hydroxy-2β-isopropoxy-17β-methoxy-5α-androstane | 26 | 100 |
| 3β-(4'-Acetylphenyl)ethynyl-3α-hydroxy-21-pyrid-4-ylthio-5β-pregnan-20-one | 29 | 94 |
| 3α-Hydroxy-5α-pregnan-20-one | 37 | 95 |
| 3α-Hydroxy-3β-methoxymethyl-21-(pyrid-4-ylthio-5α-pregan-20-one | 38 | 106 |
| 3β-Ethynyl-3α-hydroxy-21-pyrid-4-ylthio-5α-pregnan-20-one | 43 | 103 |
| 3α-Hydroxy-21-(pyrid-4-yl)oxy-5β-pregnan-20-one | 45 | 76 |
| 3β-(4'-Hydroxybutyn-1'-yl)-3α-hydroxy-17β-methoxy-5α-androstane | 47 | 104 |
| 3β-Ethynyl-3α-hydroxy-17β-methoxy-5β-androstane | 49 | 101 |
| 21-(4'-Fluorophenyl)sulfonyl-3α-hydroxy-3β-methoxymethyl-5α-pregnan-20-one | 49 | 99 |
| 3β-Ethynyl-3α-hydroxy-17β-methoxy-5β-19-norandrostane | 56 | 107 |
| 3α-Hydroxy-21-(pyrid-4-ylthio)-5β-pregnan-20-one | 59 | 74 |
| 3α-Hydroxy-17β-methoxy-5β-androstane | 62 | 106 |
| 3α-Hydroxy-17β-methoxy-3β-methoxymethyl-5α-androstane | 64 | 100 |
| 3α-Hydroxy-2β-propoxy-21-thiopropanesulfonate-5α-pregnan-20-one sodium salt | 67 | 101 |
| 3α,21-Dihydroxy-5α-pregnan-20-one(5α-ThDOC) | 76 | 100 |
| 3α-Hydroxy-3β-methyl-21-(quinolin-6-yloxy)-5═-pregnan-20-one | 76 | 96 |
| 3α-Hydroxy-21-(3'-pyridyl)oxy-5β-pregnan-20 -one | 76 | 76 |
| 3α-Hydroxy-21 -(pyrid-2-ylthio)-5β-pregnan-20 -one | 90 | 66 |
| 3β-Ethynyl-3α-hydroxy-21-(3'-hydroxypropylthio)-5β-pregnan-20-one | 93 | 97 |
| 3α-Hydroxy-17β-methoxy-3β-trifluoromethyl-5β-19-norandrostane | 93 | 115 |
| 3α-Hydroxy-17β-methoxy-3β-methyl-5α-androstane | 97 | 97 |
| 3β-(4'-Hydroxybutyn-1'-yl)-3α-hydroxy-17β-methoxy-5β-androstane 4'-hemisuccinate sodium salt | 108 | 100 |
| 3β-Ethynyl-3α-hydroxy-21-(thiopropanesulfate)-5β-pregnan-20-one sodium salt | 113 | 104 |
| 3β-Ethynyl-3α-hydroxy-17β-methoxy-5α-androstane | 122 | 106 |
| 3α-Hydroxy-2β-propoxy-21-(pyrid-4-ylthio)-5α-pregnan-20-one N-methyl iodide | 126 | 101 |
| 21-(4'-Aminophenylthio)-3α-hydroxy-3β-methoxymethyl-5α-pregnan-20-one | 127 | 89 |
| 3α-Hydroxy-2β-propoxy-21-(4'-N,N,N-trimethylammoniumphenoxy)-5α-pregnan-20 -one iodide salt | 129 | 92 |
| 3β-Ethenyl-3α-hydroxy-17β-methoxy-5α-androstane | 133 | 104 |

TABLE 1-continued

| COMPOUND | IC$_{50}$ (nM) | IMAX (%) |
|---|---|---|
| 3α-Hydroxy-21-(2'-hydroxyethylthio)-5β-pregnan-20-one | 141 | 71 |
| 3α-Hydroxy-3β-methyl-17β-(2-propynyloxy)-5α-androstane | 163 | 94 |
| 21-(4'-Fluorophenylthio)-3α-hydroxy-3β-methoxymethyl-5α-pregnan-20-one | 176 | 97 |
| 3β-Ethynyl-3α-hydroxy-21-(2'-hydroxyethylthio)-5β-pregnan-20-one | 180 | 103 |
| 3α-Hydroxy-21-(imidazo-2-ylthio)-5β-pregnan-20-one | 184 | 80 |
| 3α-Hydroxy-21-(4-pyridylmethyl)-5β-pregnan-20-one | 187 | 103 |
| 3α-Hydroxy-21-(pyrid-4-ylthio)-5α-pregnan-20-one N-methyl iodide | 188 | 100 |
| 3β-Ethynyl-3α-hydroxy-21-(3'-hydroxypropylsulfonyl)-5β-pregnan-20-one | 194 | 107 |
| 3α-Hydroxy-3β-methoxymethyl-21-(4'-pyrrolidinophenyl)sulfonyl-5α-pregnan-20-one | 208 | 101 |
| 3α-Hydroxy-17β-methoxy-3β-trifluoromethyl-5β-androstane | 216 | 103 |
| 3α-Hydroxy-21-(pyrid-4-ylsulfinyl)-5β-pregnan-20-one | 235 | 73 |
| 3α-Hydroxy-3β-methyl-21-(quinolin-6-yloxy)-5α-pregnan-20-one N-methyl iodide | 252 | 102 |
| 3α-Hydroxy-21-(4'-pyridyl)thio-5β-pregnan-20-one N-methyl iodide | 263 | 53 |
| 3α-Hydroxy-21-(3'-pyridyl)oxy-5β-pregnan-20-one N-oxide | 292 | 62 |
| 17β-[3-(4-Acetylphenyl)-2-propynyloxy]-3α-hydroxy-3β-methyl-5α-androstane | 316 | 95 |
| 3β-Ethynyl-3α-hydroxy-21-thioethanesulfate-5β-pregnan-20-one trimethylammonium salt | 322 | 101 |
| 3α-Hydroxy-17β-methoxy-3β-trifluoromethyl-5α-androstane | 341 | 100 |
| 3β-Ethynyl-3α-hydroxy-21-thiopropanesulfonate-5β-pregnan-20-one sodium salt | 343 | 97 |
| 3β-Chloromethyl-3α-hydroxy-17β-methoxy-5α-androstane | 361 | 98 |
| 3α-Hydroxy-17β-methoxy-3β-(2'-propynyl)-5α-androstane | 387 | 101 |
| 3α-Hydroxy-2β-isopropoxy-5α-androstane | 456 | 98 |
| 3β(4'-Acetylphenyl)ethynyl-3α-hydroxy-19-nor-5β-androstane | 492 | 99 |
| 3α-Hydroxy-5α-androstane | 494 | 99 |
| 3α-Hydroxy-17β-(2-hydroxyethoxy)-5α-androstane | 534 | 99 |
| 3β-Ethynyl-3α-hydroxy-21-thioethanesulfonate-5β-pregnan-20-one sodium salt | 607 | 93 |
| 3α-Hydroxy-21-sulfonic acid-5β-pregnan-20-one 21-sodium salt | 732 | 62 |
| 3β-Ethynyl-3α-hydroxy-21-(3'-hydroxypropylsulfinyl)-5β-pregnan-20-one | 782 | 107 |
| 3α-Hydroxy-5β-androstane | 815 | 83 |
| 3α-Hydroxy-2β-propoxy-21-sulfonylpropanesulfonate-5α-pregnan-20-one sodium salt | 1023 | 101 |
| 3β-Ethynyl-3α-hydroxy-21-(3'-thiopropionate)-5β-pregnan-20-one sodium salt | 1025 | 101 |
| 3α-Hydroxy-5α-androstan-17-one 17-ketal | 1030 | 99 |
| Progesterone | 5200 | 100 |
| 3β-Hydroxy-5α-pregnan-20-one (Allopregnanolone) | >10$^6$ | 33 |
| 4-Pregnan-11β,21-diol-3,20-dione (Corticosterone) | >10$^6$ | 30 |
| 17β-Estradiol | not active | 0 |
| Cholesterol | not active | 0 |

As can be seen from Table 1, 3α-hydroxy-5α-pregnan-20-one, 3α,21-dihydroxy-5α-pregnan-20-one and compounds of the present invention have low IC$_{50}$, which is the concentration necessary to achieve 50% maximal inhibition of [$^{35}$S]TBPS binding, while compounds such as sex steroids (R5020, estradiol and progesterone), glucocorticoids (corticosterone) and cholesterol having a high IC$_{50}$ are essentially inactive. Thus, it is anticipated that hormonal steroids and cholesterol per se will not have any therapeutic value for the indications described herein. In order to distinguish this unique class of steroids from hormonal steroids, they are now termed "neuroactive steroids." However, sex steroids such as progesterone can be metabolized in the body to steroids similar to 3α-hydroxy-5α-pregnan-20-one. Thus, progesterone can be considered as a "neuroactive steroid" prodrug. The TBPS data correlates well with data on $^{36}$Cl ion uptake-potentiated by various 3α-hydroxylated steroids described in Purdy R. H., et al., *J. Med. Chem* 33:1572–1581 (1990). These data also correlate well with electrophysiological data obtained by measuring steroid's activity to potentiate GABA-induced current in oocytes injected with human GABA receptors as described in Hawkinson, J. E. et al., *Mol. Pharmacol.* 46:977–985 (1995). This indicates that the TBPS assay is an approximate measurement of steroids ability to allosterically modulate Cl channel activity.

Compounds with Limited Efficacy

In as much as the desired therapeutic activity should be available to the patient with the least undesirable side effects, this invention also involves the discovery of novel agonists with partial activity. (Table 1, compounds with I$_{max}$ <100%). For the patients who desire amelioration of anxiety or convulsions, hypnosis is undesired. For the patients who desire amelioration of insomnia, anesthetic effects are undesirable. The compounds described as agonists with partial activity are expected to provide the desired effect with minimal undesired side effects.

Benefits Over Progesterone

The correlations between reduced levels of progesterone and the symptomns associated with PMS, PND, and catamenial epilepsy (Backstrom, T. et al., *J. Psychosom. Obstet. Gynaecol.* 2:8–20 (1983)); Dalton, K., *Premenstrual Syndrome and Progesterone Therapy*, 2nd edition, Chicago Yearbook, Chicago (1984)) led to the use of progesterone in their treatment (Mattson et al., "Medroxyprogesterone therapy of catamenial epilepsy," in *Advances in epileptology: XVth Epilepsy International Symposium*, Raven Press, New York (1984), pp. 279–282; Dalton, K., *Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks, et al (1986). These results are predictable when considered in light of the results of our in vitro studies which demonstrate that progesterone has very low potency at the GRC, as seen in Table 1, compared to neuroactive steroids described in this invention.

The beneficial effect of progesterone is probably related to the variable conversion of progesterone to the active progesterone metabolites which act at the $GABA_A$ receptor. The use of specific neuroactive steroids in the treatment of the aforementioned syndromes is clearly superior to the use of progesterone based upon the high potency and efficacy of these compounds (See Gee, K. W. et al., *European Journal of Pharmacology*, 136:419–423 (1987) and the Table 1, above).

No Hormonal Side Effects

It has also been demonstrated that neuroactive steroids lack hormonal side effects by the lack of affinity for the progesterone and other hormonal steroid receptors (Tables 2–5). The data presented were obtained by performing assays in accordance with the procedures previously described to determine the effect of progesterone metabolites and their derivatives and the progestin R5020 on the binding of [$^3$H]R5020 to the progesterone receptor in rat uterus (Gee et al., *Journal of Pharmacology and Experimental Therapeutics* 246:803–812 (1988).

$^3$H-progesterone (0.15 nM) was incubated with the rat uterus cytosol in the presence of the test compounds. The specific bindings were determined after incubation and compared to the control incubation without the compounds. The data are expressed as percent inhibition of binding. If the compounds bind to the progesterone receptor with high affinity, a 100% inhibition of binding would be expected at the concentration tested.

Various hormonal activities of representative neuroactive steroids were further studied through testing their potential estrogenic, mineralocorticoid and glucocorticoid activities. These activities were analyzed by monitoring the ability of the compounds to inhibit binding of the steroid hormones to their respective hormone receptors. The results are shown in Tables 3–5. They are expressed as percent inhibition of $^3$H-ligand binding to the various steroid hormone receptors for the compounds at $10^{-6}$ M. Control values are represented by the binding in the absence of testing compounds.

In Table 4, rats were adrenalectornized 3 days prior to sacrifice. To isolate the mineralocorticoid receptor, brain cytosol fractions were prepared as described in Gee et al., *Journal of Pharmacology and Experimental Therapeutics* 246:803–812 (1988). The drugs were incubated with 3 nM of $^3$H-aldosterone (the specific ligand for the mineralocorticoid receptor) in the presence of the selective type II agonist RU28362 (0.5 μM) which blocks $^3$H-aldosterone binding to the type II (glucocorticoid) receptors.

TABLE 2

Inhibition of $^3$H-Progesterone Binding to the Bovine Uteral Progesterone Receptors

| Competitor ($10^{-6}$M) | % of Inhibition |
|---|---|
| R5020 | 100 |
| 5α-pregnan-3α-ol-20-one | 14 |
| 5α-pregnan-3α,21-diol-20-one | 13 |
| 5α-pregnan-3α,20-diol | 6 |
| 5α-pregnan-3α-ol-3β-methyl-20-one | 4 |
| 5β-pregnan-3α,21-diol-20-one | 6 |
| 5α-pregnan-3β,20-trimethyl-3α,20-diol | 8 |
| 5β-pregnan-3α,20α-diol | 0 |
| 5β-pregnan-3α-of-20-one | 9 |
| 5α-pregnan-20-dimethyl-3α,20-diol | 0 |

TABLE 3

Inhibition of $^3$H-Aldosterone Binding to Hippocampal Mineralocorticoid Receptors

| Competitor ($10^{-6}$M) | % of Inhibition |
|---|---|
| Aldosterone | 95.5 |
| 5α-pregnan-3α,21-diol-20-one | 76.7 |
| 5β-pregnan-3α,21-diol-20-one | 13.8 |
| 5α-pregnan-3α,ol-20-one | 0 |
| 5β-pregnan-3α,ol-20-one | 0 |
| 5α-pregnan-3α,20α-diol | 0 |
| 5β-pregnan-3α,20α-diol | 0 |
| 5α-pregnan-3α,20-diol-20-dimethyl | 0 |
| 5α-pregnan-3α-ol-3β-methyl-20-one | 3.2 |
| 5α-pregnan-3β,20-trimethyl-3α,20-diol | 0 |

For Table 4, brain cytosol fractions were prepared as for Table 3, and the compounds were incubated with 3 nM of $^3$H-dexamethasone (the specific ligand for the glucocorticoid receptor).

TABLE 4

Inhibition of $^3$H-Dexamethasone Binding to Glucocorticoid Receptors

| Competitor ($10^{-6}$M) | % of Inhibition |
|---|---|
| Dexamethasone | 100 |
| 5α-pregnan-3α,21-diol-20-one | 29.5 |
| 5β-pregnan-3α,21-diol-20-one | 8.2 |
| 5α-pregnan-3α,ol-20-one | 8.7 |
| 5β-pregnan-3α,ol-20-one | 5.9 |
| 5α-pregnan-3α,20α-diol | 2.6 |
| 5β-pregnan-3α,20α-diol | 1.4 |
| 5α-pregnan-20-dimethyl-3α,20-diol | 2.6 |
| 5α-pregnan-3α,ol-3β-methyl-20-one | 0.6 |

Table 5 shows the inhibition of $^3$H-estradiol (the specific ligand for the estrogen receptor) binding to bovine uteri cytosol, prepared as previously described (Gee et al., *Journal of Pharmacology and Experimental Therapeutics* 246.803–812 (1988)). $^3$H-Estradiol (0.15 nM) was incubated with the cytosol in the presence of the compounds.

TABLE 5

Inhibition of $^3$H-Estradiol Binding to Bovine Uteral Estrogen Receptors

| Competitor ($10^{-6}$M) | % of Inhibition |
|---|---|
| 17β-estradiol | 100 |
| 5α-pregnan-3α-ol-20-one | 0 |

TABLE 5-continued

Inhibition of $^3$H-Estradiol Binding to Bovine Uteral Estrogen Receptors

| Competitor (10$^{-6}$M) | % of Inhibition |
|---|---|
| 5α-pregnan-3α,21-diol-20-one | 2 |
| 5α-pregnan-3α,20α-diol | 0 |
| 5α-pregnan-3α-ol-3-methyl-20-one | 0 |
| 5β-pregnan-3α,21-diol-20-one | 0 |
| 5α-pregnan-3β,20 -trimethyl-3α,20-diol | 0 |
| 5β-pregnan-3α,20α-diol | 8 |
| 5β-pregnan-3α-ol-20 -one | 0 |
| 5α-pregnan-20-dimethyl-3α,20-diol | 0 |

The results of these expeziments clearly show that neuroactive steroids do not have a strong affinity for any of the above mentioned steroid receptors. Thus, they wil not have the hormonal side-effects which would be associated with binding to such steroid receptors. The neuroactive steroid, 3α-hydroxy-3β-methyl-5α-pregnan-20-one, was further tested in vivo and was also found not to have any hormonal activity when given to animals in vivo.

Anti-Convulsant Activity

Experiments were also performed to determine the physiological relevance of neuroactive steroid and GABA receptor interactions by assessing the ability of compounds of the present invention to prevent metrazol induced convulsions in mice. Mice were injected with various doses of the test compounds of the invention, 10 minutes prior to the injection of metrazol. The time to onset of myoclonus (presence of forelimb clonic activity) induced by metrazol was determined by observing each mouse for a period of 30 minutes. In control mice, metrazol (85 mg/kg) will induce convulsion in 95% of the animals. The ability of several compounds of the present invention to protect mice from convulsion is shown in Table 6.

TABLE 6

Antimetrazol Activity in Mice

| Compound | Route | Vehicle | Dose (mg/kg) | % Protected |
|---|---|---|---|---|
| 3β-(4'-Acetylphenyl)ethynyl-3α-hydroxy-17β-methoxy-5β-androstane | IP | 50% hpbcd | 10 | 25 |
| 3β-(4'-Acetylphenyl)ethynyl-3α-hydroxy 17β-methoxy-5β-19-norandrostane | IP | 50% hpbcd | 10 | 31 |
| 3α-Hydroxy-3β-(4'-hydroxybutyn-1-yl)-17α-methoxy-5β-androstane | IP | 50% hpbcd | 10 | 50 |
| 3α-Hydroxy-3β-(4'-hydroxybutyn-1-yl)-17β-methoxy-5β-androstane | IP | 50% hpbcd | 10 | 75 |
| 3α-Hydroxy-3β-(2'-propynyl)-17β-methoxy-5α-androstane | IP | 50% hpbcd | 10 | 12.5 |
| 3β-Chloromethyl-3α-hydroxy-17β-methoxy-5α-androstane | IP | 50% hpbcd | 10 | 12.5 |
| 3β-Methoxymethyl-3α-hydroxy-17β-methoxy-5α-androstane | IP | 50% hpbcd | 10 | 87.5 |
| 3α-Hydroxy-3β-ethenyl-17β-methoxy-5α-androstane | IP | 50% hpbcd | 10 | 87.5 |
| 3α-Hydroxy-3β-ethenyl-17β-methoxy-5α-androstane | IP | 50% hpbcd | 10 | 62.5 |
| 3α-Hydroxy-3β-trifluoromethyl-17β methoxy-5β-androstane | IP | 50% hpbcd | 10 | 37.5 |
| 3α-Hydroxy-3β-ethynyl-17β-methoxy-5β-androstane | IP | 50% hpbcd | 10 | 50 |
| 3α-Hydroxy-3β-ethynyl-17β-methoxy-5β-androstane | IP | 50% hpbcd | 10 | 50 |
| 3α-Hydroxy-3β-(4'-hydroxybutyn-1-yl)-17β-methoxy-5β-androstane 4'-hemisuccinate sodium salt | IP | water | 10 | 75 |
| 3α-Hydroxy-21-(pyrid-4-ylthio)-5α-pregnan-20-one | IP | 50% hpbcd | 10 | 62.5 |
| 3α-Hydroxy-21-(pyrid-4-ylthio)-5β-pregnan-20-one | IP | 50% hpbcd | 10 | 75 |
| 3α-Hydroxy-21-(pyrid-2-ylthio)-5β-pregnan-20-one | IP | 50% hpbcd | 20 | 12.5 |
| 3α-Hydroxy-21-(imidazo-2-ylthio)-5β-pregnan-20-one | IP | 50% hpbcd | 10 | 6.25 |
| 3α-Hydroxy-21-(pyrid-4-ylsulfinyl)-5β-pregnan-20-one | IP | 50% hpbcd | 10 | 25 |
| 3β-Ethynyl-3α-hydroxy-21-thioethanesulfonate-5β-pregnan-20 -one sodium salt | IP | 50% hpbcd | 10 | 0 |
| 3α-Hydroxy-3β-(4-hydroxybutynyl)-21-(pyrid-4-ylthio)-5β-pregnan-20-one | IP | 50% hpbcd | 10 | 50 |
| 3α-Hydroxy-21-(2'-hydroxyethylthio)-5β-pregnan-20-one | IP | 50% hpbcd | 10 | 12.5 |
| 3α-Hydroxy-3β-(3'-methylbut-3'-en-1'-ynyl)-17β-methoxy-5β-androstane | IP | 50% hpbcd | 10 | 87.5 |

TABLE 6-continued

Antimetrazol Activity in Mice

| Compound | Route | Vehicle | Dose (mg/kg) | % Protected |
|---|---|---|---|---|
| 20,20-[2',3'-Bis(carboxy)ethylenedioxy]-3α-hydroxy-3β-trifluoromethyl-5β-19-norpregnane dipotassium salt | PO | 10% hpbcd | 10 | 25 |

The ability of synthetic neuroactive steroids to protect animals against other chemical convulsants was further demonstrated for several compounds of the present invention. The anticonvulsant tests are similar to that described above. The following chemical convulsants were employed: metrazol (85 mg/kg); (suculline (2.7 mg/kg); picrotoxin (3.15 mg/kg); strychnine (1.25 mg/g); or vehicle (0.9% saline). Immediately after the injection of convulsant or vehicle, the mice were observed for a period of 30 to 45 minutes. The number of animals with tonic and/or clonic convulsions was recorded. In the maximal electroshock test, 50 mA of current at 60 Hz was delivered through corneal electrodes for 200 msec to induce tonic seizure. The ability of compounds to abolish the tonic component was defined as the endpoint General CNS depression potential was determined by a rotorod test 10 minutes after the injection of compounds where the number of mice staying on a rotating (6 rpm) rod for 1 minute in one of the three trials was determined. The $ED_{50}$'s (the dose at which the half-maximal effect occurs) were determined for each screen and are presented in Table 7, infra. The results demonstrate that neuroactive steroids, in comparison to other clinically useful anti-convulsants, are highly effective with profiles similar to that of the BZ clonazepam. These observations demonstrate the therapeutic utility of these compounds as modulators of brain excitability, which is in correspondence with their high affinity interaction with the GRC in vitro.

TABLE 7

Anticonvulsant Activity in Mice

| | $ED_{50}$ (mg/Kg) | | | | | |
|---|---|---|---|---|---|---|
| Compound | RR | MES | PTZ | BIC | TBPS | STR |
| 3α-Hydroxy-3β-methyl-5α-pregnan-20 one[a] | 33.4 | 29.7 | 4.3 | 4.6 | 11.7 | >40 |
| 3α-hydroxy-17β-methoxy-5β-androstane | — | 87.5[b] | 87.5[c] | — | — | — |
| 3β-Methoxymethyl-3α-hydroxy-17β-methoxy-5α-androstane | — | 18.7[b] | 87.5[c] | — | — | — |
| 3α-Hydroxy-3β-ethynyl-17β-methoxy-5β-androstane | — | 31.2[b] | 50[c] | — | — | — |
| 3β-(4'-Acetylphenyl)ethynyl-3α-hydroxy-17β-methoxy-19-nor-5β-androstane | — | 25[b] | 12.5[c] | — | — | — |
| Clonazepam[d] | 0.184 | 111 | 0.025 | 0.0046 | 205 | >300 |
| Phenobarbital[d] | 69 | 22 | 13 | 38 | ND | 95 |
| Phenytoin[d] | 65 | 10 | NP | NP | ND | — |
| Valproate[d] | 514 | 272 | 154 | 360 | ND | 293 |
| Progabide[e] | — | 75 | 30 | 30 | ND | 75 |

The abbreviations are RR (Rotorod); MES (maximal electroshock); PTZ (metrazol); BIC (bicuclline); PICRO (picrotoxin); STR (strychnine); NP (no protection)
[a]Dissolved in 50% hydroxypropyl-β-cyclodextrin in water. The route of administration for steroids and convulsants was i.p. and s.c., respectively.
[b]% Protected, 20 mg/kg, i.p., 10 min 50% hpbcd.
[c]% Protected, 10 mg/kg, i.p., 10 min 50% hpbcd.
[d]Anticonvulsant data are from Swinyard & Woodhead, General principles: experimental detection, quantification and evaluation of anticonvulsants, in Antiepileptic Drugs, D.M. Woodbury, J.K. Penry, and C.E. Pippenger, eds. p. 111, (Raven Press, New York), 1982.
[e]The chemical convulsants in the progabide studies were administered i.v., all data from Worms et al., Gamma-aminobutyric acid (GABA) receptor stimulation. I. Neuropharmacological profiles of progabide (SL 76002) and SL 75102, with emphasis on their anticonvulsant spectra, Journal of pharmacology and Experimental Therapeutics 220: 660–671 (1982).

Anxiolytic Effects

The following experiments demonstrate that the compounds of the present invention are effective anxiolytics in two animal models of human anxiety that measure the behavioral effects of anxiolytic compounds. Data on other compounds of the present invention in these measurements is presented in Tables 8 and 9. The two animal models used to measure the behavioral effects of anixiolytic compounds are the elevated plus-maze test and the Geller-Seifter conflict test.

A. Elevated PLus-Maze Test

The theoretical basis for the elevated plus-maze test is similar to that of the fight/dark transition test. As it was described previously by Pellow et al. *J. Neurosci. Meth.* 14:149–167 (1985)), the elevated plus-maze apparatus is designed to utilize the mice's natural aversion to open spaces. The apparatus consists of two open-arms and two enclosed-arms. The elevated plus-maze test allows for two measures of anxiety, the number of entries into the open-arms and the time spent on the open-arms, both expressed as a percentage of the total number of entries and time spent in/on both the open-arms and enclosed-arms.

Male N.I.H Swiss-Webster mice (Harlan, Indianapolis, Ind.) weighing 15–20 g were housed four per cage in polyethylene cages with sawdust bedding. The colony room was environmentally controlled (22° C.) with a 12 hr light/dark cycle (0600–1800 hr). Food and water were available ad libitum, except during testing. The experiments were run from 0700–1500 hr and groups were counterbalanced for time of day effects. Mice were only administered drug or vehicle once.

The method used was previously described (Lister, *Psychopharmacol.* 92:180–185 (1987)). The apparatus included two open arms perpendicular to two enclosed arms elevated 50 cm from the floor. Each arm was 50 cm long and the walls of the enclosed arms were 40 cm tall. The maze was made completely of black plexiglass. Incandescent 200 W light bulbs were above each of the open arms to produce a strong contrast between the open arms and the enclosed arms.

Ten minutes after an injection, the N.I.H. Swiss-Webster mice were placed in the center of the plus-maze facing an open arm. During the 5 min test period, the number of entries onto the open arms and the enclosed arms, and the time spent in the open arms and enclosed arms were measured. All four paws had to be within an arm for the dependent variable to be measured. Therefore, the time spent in the center of the maze is not counted, so the total time spent in the open arms and the enclosed arms may not equal 5 min.

Table 8 shows the summary of anxiolytic activities of compounds of the present invention using the elevated plus-maze under the same conditions described above.

TABLE 8

| Compound | Route | Vehicle | Dose (mg/kg) | Plus-Maze (% Control)* |
|---|---|---|---|---|
| 3$\beta$-(4'-Acetylphenyl)ethynyl-3$\alpha$-hydroxy-17$\beta$-methoxy-5$\beta$-androstane | IP | 50% hpbcd | 10 | 129 |
| 3$\beta$-(4'-Acetylphenyl)ethynyl-3$\alpha$-hydroxy-17$\beta$-methoxy-5$\beta$-19-norandrostane | IP | 50% hpbcd | 10 | 156 |
| 3$\alpha$-Hydroxy-3$\beta$-(4'-hydroxybutyn-1-yl)-17$\beta$-methoxy-5$\alpha$-androstane | IP | 50% hpbcd | 10 | 158 |
| 3$\alpha$-Hydroxy-3$\beta$-ethynyl-17$\beta$-methoxy-5$\beta$-19-norandrostane | IP | 50% hpbcd | 10 | 158 |
| 3$\alpha$-Hydroxy-17$\beta$-methoxy-5$\beta$-androstane | IP | 50% hpbcd | 10 | 115 |
| 3$\beta$-Ethynyl-3$\alpha$-hydroxy-17$\beta$-methoxy-5$\alpha$-androstane | IP | 50% hpbcd | 10 | 129 |
| 3$\beta$-Methoxymethyl-3$\alpha$-hydroxy-17$\beta$-methoxy-5$\alpha$-androstane | IP | 50% hpbcd | 10 | 130 |
| 3$\alpha$-Hydroxy-3$\beta$-ethenyl-17$\beta$-methoxy-5$\alpha$-androstane | IP | 50% hpbcd | 10 | 127 |
| 3$\alpha$-Hydroxy-3$\beta$-trifluoromethyl-17$\beta$-methoxy-5$\beta$-androstane | IP | 50% hpbcd | 10 | 115 |
| 3$\alpha$-Hydroxy-3$\beta$-trifluoromethyl-17$\beta$-methoxy-5$\beta$-19-norandrostane | IP | 50% hpbcd | 10 | 107 |
| 3$\alpha$-Hydroxy-3$\beta$-ethynyl-17$\beta$-methyoxy-5$\beta$-androstane | IP | 50% hpbcd | 10 | 123 |
| 3$\alpha$-Hydroxy-21-(pyrid-4-ylthio)-5$\alpha$-pregnan-20-one | IP | 50% hpbcd | 10 | 148 |
| 3$\alpha$-Hydroxy-21-(pyrid-4-ylthio)-5$\beta$-pregnan-20-one | IP | 50% hpbcd | 10 | 151 |
| 3$\alpha$-Hydroxy-21-(pyrid-2-ylthio)-5$\beta$-pregnan-20-one | IP | 50% hpbcd | 20 | 187 |
| 3$\alpha$-Hydroxy-21-(imidazo-2-ylthio)-5$\beta$-pregnan-20-one | IP | 50% hpbcd | 10 | 166 |
| 3$\alpha$-Hydroxy-21-(pyrid-4-ylsulfinyl)-5$\beta$-pregnan-20-one | IP | 50% hpbcd | 10 | 171 |
| 3$\beta$-Ethynyl-3$\alpha$-hydroxy-21-thioethanesulfonate-5$\beta$-pregnan-20-one sodium salt | IP | 50% hpbcd | 10 | 127 |
| 3$\alpha$-Hydroxy-3$\beta$-(4'-hydroxybutyn-1-yl)-17$\beta$-methoxy-5$\beta$-androstane 4'-hemisuccinate sodium salt | PO | water | 10 | 309 |

*The percent of control on the time spent on the open-arms

B. Geller-Seifter Conflict Test

This animal model of human anxiety utilizes a conditioned state of conflict in rats to ascertain the anxiolytic properties of drugs. Rats are conditioned to bar press for positive reinforcement under two schedules of behavior (Geller and Seifter, *Psychopharmacologia* 1:482–492 (1960)). The first includes bar pressing under a variable ratio schedule without punishment. The second component is a fixed ratio schedule with each bar press resulting in a positive reinforcement and a punishment The punished component produces a state of conflict within the animal. The unpunished component allows for the observation of any response depressant effects a drug may possess. An anxiolytic response would increase the punished responding without affecting the unpunished responding.

Male albino Sprague-Dawley rats (Charles River Labs, Wilmington, Mass.) weighing 250–300 g were used for conflict experiments and were kept on a restricted diet of Purina Lab Chow food pellets with water available at all times to maintain body weight at 85% of their free-feeding young adult levels. Rats were housed individually under a 12-hour light dark cycle with lights on from 0700–1900.

The ant-anxiety (punishment-lessening) and response depressant effects of compounds of the present invention were measured in rats by the conflict test of Geller and Seifter. In this 63-min test hungry rats perform a lever-press response to obtain a sweetened milk reward. The reinforcement schedule consists of punishment and nonpunishment components, alternating approximately every 15 min. Rats were trained in test chambers (Coulbourn instruments) with a lever mounted in one wall, a small dipper that delivered the 0.1-mL milk reward (1 part Eagle condensed milk:2 parts water), and a metal grid floor through which the foot-shock punishment was administered. A DEC PDP 11/73 minicomputer running SKED (State Systems) was used for programming and recording.

Rats initially learned to respond on a continuous reinforcement schedule and progressed rapidly to 30-sec, 1-min, and 2-min variable interval (VI) schedules. On the continuous reinforcement schedule, rats received milk reward following every lever press; on the VI schedules, milk rewards were available at infrequent and variable intervals, eventually at an average of once every 2 min. Four 3-min "conflict" periods were then introduced on the unpunished VI baseline; the first started after 3 min of VI performance and the others were alternated between 12-min periods of VI responding. During conflict periods, which were signalled by the presentation of a light and a tone, the continuous reinforcement schedule was again in force and each lever press delivered both a milk reward and a brief (0.25 msec) foot-shock punishment. Shock intensity was 0.2 mA initially, and was increased daily in increments of 0.02 mA in order to gradually suppress lever pressing to 5 responses or less per conflict period. This training took 4–6 weeks, after which stable low rates of response were observed during conflict periods and stable high rates in the nonpunishment periods. Drug-induced increases in the rate of punished responses were taken as an index of antianxiety activity, while decreases in the rate of unpunished responses were taken as an index of response depression or sedation.

Table 9 shows the summary of antiolytic activities of a compound of the present invention in the Geller-Seifter test under the experimental conditions described above. The remaining compounds of the present invention are likewise expected to produce increases in the rate of punished responses in the Geller-Seifter test, and expected to possess anxiolytic activity.

TABLE 9

Anxiolytic Activity in Geller/Seifter in Rats

| Compounds | Route | Vehicle | Dose (mg/kg) | Geller/Seifter (% or control) |
|---|---|---|---|---|
| 3α-Hydroxy-3β-methoxymethyl-5α-pregnan-20-one | IP | 50% hpbcd | 10 | 958 |
| 11α-N,N-Dimethylamino-3α-hydroxy-3β-trifluoromethyl-5β-pregnan-20-one | IP | citrate | 20 | 145 |
| Sodium S-(3α-hydroxy-3β-methoxymethyl-5α-pregnan-20-on-21-yl)thiosulfate | PO | water | 32 | 4487.5 |
| 3α-Hydroxy-3β-ethoxymethyl-5α-pregnan-20-one | IP | 50% hpbcd | 40 | 3743 |

Prodrugs

Anti-convulsant activity of a prodrug (3α isobutyric ester) of the basic compound 3α-hydroxy-17β-methoxy-5α-androstane is shown in FIG. 1.

Percent protection by this prodrug of 3α-hydroxy-17β-methoxy-5α-androstane against metrazol-induced seizures was plotted against time after administration of the compounds (FIG. 1). It is understood that this compound is used as an experimental example to illustrate the utility of prodrugs. In contrast to benzodiazcpines, neuroactive steroids can also induce anesthesia. Their ability to induce anesthesia is thought to be due to their ability to open the chloride ion channel in the absence of GABA, which is a property not possessed by benzodiazepines. Therefore, neurosteroids can act directly in the absence of GABA, at the receptor, and also "indirectly", in the presence of GABA. This "indirect" action is called "modulating" the receptor. Lambert et al., Trends Pharmacology Science 8: 224–227 (1987).

The compounds of and used in the invention can also be used for anesthetic indications at high doses. However, the preferred route of administration to induce anesthesia is intravenous (i.v.) administration. In animals, a drug's anesthetic properties is measured by the drug's ability to produce a loss-of-righting reflex. The loss-of-righting reflex is defined as the inability of an animal to right itself within 30 seconds when placed on its back. Mice were administered drug i.v. in the lateral tail vein. Following administration, mice were placed on their backs and observed for loss-of-righting reflex. Illustrative results are presented in Table 10.

TABLE 10

Anesthetic Activity in Mice

| Compounds | Route | Vehicle | Dose (mg/kg) | Loss-of-Righting Reflex (%) |
|---|---|---|---|---|
| 3α-Hydroxy-17β-methoxy-3β-(3' methyl-but-3'-en-1'-ynyl)-5β-androstane | iv | 50% hpbcd | 10 | 100 |
| 3β-Ethynyl-3α-hydroxy-17β-methoxy-5β-androstane | iv | 50% hpbcd | 10 | 50 |

TABLE 10-continued

Anesthetic Activity in Mice

| Compounds | Route | Vehicle | Dose (mg/kg) | Loss-of-Righting Reflex (%) |
|---|---|---|---|---|
| 3β-Ethynyl-3α-hydroxy-17β-methoxy-5β-19-nor-androstane | iv | 50% hpbcd | 10 | 100 |
| 3α-Hydroxy-17β-methoxy-3β-methoxymethyl-5α-androstane | iv | 10% hpbcd | 10 | 50 |
| 3α-Hydroxy-17β-methoxy-3β-trifluoromethyl-5β-19-nor-androstane | iv | 50% hpbcd | 10 | 62.5 |
| 3α-Hydroxy-17β-methoxy-3β-trifluoromethyl-5β-androstane | iv | 10% hpbcd | 20 | 37.5 |
| 3α-Hydroxy-5α-pregnan-11,20-dione (Alphaxalone) | iv | 50% hpbcd | 10 | 37.5 |

It is anticipated that prodrugs, with similar modifications as described above, of compounds of and used in the invention will have activity as prodrugs.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of the formula:

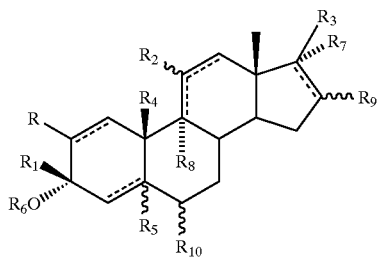

or a physiologically acceptable salt or 3-ester thereof; wherein

R is one of hydrogen, amino, thio, sulfinyl, sulfonyl, halogen, lower alkoxy, alkynyl or substituted alkynyl;

$R_1$ is one of hydrogen, alkyl, alkenyl, alkynyl, haloalkyl, dihaloalkyl, trihaloalkyl, optionally substituted aralkynyl, alkoxyalkyl, aminoalkyl, cyano, cyanoalkyl, thiocyanoalkyl, azidoalkyl, optionally substituted arylalkyl, arylalkenyl, optionally substituted aryl, optionally substituted aralkylalkynyl, alkanoyloxyalkynyl, optionally substituted heteroaryloxyalkynyl, oxoalkynyl or a ketal thereof, cyanoalkynyl, optionally substituted heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_2$ is one of hydrogen, alkoxy, a keto group or a dimethylamino group;

$R_3$ is one of —C(O)—$CH_2$—O—D or —C(O)—$CH_2$—Y'—Z—G;

Y' is O;

Z is one of unsubstituted alkylene, alkenylene or alkynylene;

G is one of C-attached heteroaryl or a quaternary ammonium salt of a nitrogen containing heteroaryl group;

D is C-attached heteroaryl or a quaternary ammonium salt of a nitrogen containing heteroaryl group;

$R_4$ is one of hydrogen or methyl;

$R_5$, $R_6$, $R_7$, $R_8$, $R_9$ and $R_{10}$ are each hydrogen; and the dotted lines all represent single bonds;

wherein said C-attached heteroaryl is selected from the group consisting of pyridyl, pyrimidinyl, pyrazinyl, imidazolyl, triazolyl, tetrazolyl, quinolinyl, indolyl, benzimidazolyl, and isoquinolinyl.

2. A compound of claim 1, wherein R is hydrogen, halogen, lower alkoxy, or alkynyl optionally substituted by lower acyclic alkyl, lower cyclic alkyl, carboaryl, heteroaryl, alkenyl, alkynyl, alkoxy, halo, haloalkyl, amino, mercapto, alkylthio, alkylsulfinyl, alkylsulfonyl, nitro, alkanoyl, aklanoyloxy, alkanoyloxyalkanoyl, alkoxycarboxy, formyl, carboxy, hydroxy, cyano, azido, keto, alkanoylamido, heteroaryloxy, heterocarbocyclicoxy, —$CONR^k R^l$, where $R^k$ and $R^l$ are independently hydrogen or lower alkyl, —$COOR^j$, wherein $R^j$ is lower alkyl, or combinations thereof.

3. The compound of claim 1, wherein $R_3$ is —C(O)—$CH_2$—O—D.

4. The compound of claim 1, wherein $R_3$ is —C(O)—$CH_2$—Y'—Z—G.

5. A compound of claim 1, wherein:

R is hydrogen, halogen, lower alkoxy, alkynyl or substituted alkynyl; and $R_3$ is one of —C(O)—$CH_2$—O—D or —C(O)—$CH_2$—Y'—Z—G.

6. A compound of claim 5, wherein $R_3$ is —C(O)—$CH_2$—O—D.

7. A compound selected from the group consisting of 3α-hydroxy-3β-methyl-21-(quinolin-6-yloxy)-5α-pregnan-20-one N-methyl iodide; and 3α-hydroxy-3β-methyl-21-(quinolin-6-yloxy)-5α-pregnan-20-one.

8. A pharmaceutical composition comprising a compound of claim 1, and a pharmaceutically acceptable carrier.

9. A pharmaceutical composition comprising a compound of claim 7 and a pharmaceutically acceptable carrier.

* * * * *